(12) United States Patent
Brown et al.

(10) Patent No.: US 8,119,804 B2
(45) Date of Patent: *Feb. 21, 2012

(54) ORGANIC SEMICONDUCTING LAYERS

(75) Inventors: Beverley Anne Brown, Warrington (GB); Janos Veres, Manchester (GB); Remi Manouk Anemian, Cheadle (GB); Richard Williams, Manchester (GB); Simon Dominic Ogier, Sowerby Bridge (GB); Stephen William Leeming, Manchester (GB)

(73) Assignee: Merck Patent GmbH, Darmstadt (DE)

( * ) Notice: Subject to any disclaimer, the term of this patent is extended or adjusted under 35 U.S.C. 154(b) by 23 days.

This patent is subject to a terminal disclaimer.

(21) Appl. No.: 12/719,545

(22) Filed: Mar. 8, 2010

(65) Prior Publication Data

US 2010/0227956 A1    Sep. 9, 2010

Related U.S. Application Data

(63) Continuation of application No. 10/580,552, filed on May 26, 2006, now Pat. No. 7,842,942.

(30) Foreign Application Priority Data

| Nov. 28, 2003 | (GB) | ..................................... 0327654 |
| Apr. 7, 2004 | (GB) | ..................................... 0407852 |
| Jun. 26, 2004 | (GB) | ..................................... 0414347 |

(51) Int. Cl.
    *C07D 471/00*    (2006.01)
(52) U.S. Cl. .................. 546/49; 257/E51.025; 257/40; 549/41; 552/220; 556/489
(58) Field of Classification Search .................. 546/49; 257/E21.025, 40; 549/41; 552/220; 556/489
    See application file for complete search history.

(56) References Cited

U.S. PATENT DOCUMENTS

| 5,936,259 | A | 8/1999 | Katz et al. |
| 5,939,236 | A | 8/1999 | Pavelchek et al. |
| 6,309,790 | B1 | 10/2001 | Jung et al. |
| 6,855,949 | B2 | 2/2005 | De Leeuw et al. |
| 6,864,396 | B2 | 3/2005 | Smith et al. |
| 7,061,010 | B2 | 6/2006 | Minakata |
| 7,095,044 | B2 | 8/2006 | Brown et al. |
| 7,557,370 | B2 * | 7/2009 | Li et al. ............................ 257/40 |
| 2003/0067005 | A1 | 4/2003 | De Leeuw et al. |
| 2003/0151026 | A1 | 8/2003 | Hanna et al. |
| 2004/0038459 | A1 | 2/2004 | Brown et al. |

FOREIGN PATENT DOCUMENTS

| JP | 05055568 | 3/1993 |
| JP | 2001-242808 | 9/2002 |
| WO | WO 0245184 | 6/2002 |
| WO | WO 03016599 | 2/2003 |
| WO | WO 03030278 | 4/2003 |

OTHER PUBLICATIONS

Sheraw, Jackson, Eaton, Anthony: "Functionalized Pentacene Active Layer Organic Thin-Film Transistors" Advanced Materials, vol. 15, No. 32, Oct. 15, 2003 pp. 2009-2011, XP002321980.

Anthony, Eaton, Parkin: "A Road Map to Stable, Soluble, Easily Crystallized Pentacene Derivatives" Organic Letters, vol. 4, No. 1, Dec. 15, 2001, pp. 15-18, XP002427517.

Anthony, Brooks, Eaton, Matson, Parkin: "Synthesis, properties and device applications of functionalized acenes" Proceedings of the SPIE, vol. 5217, Aug. 3, 2003,—2003 pp. 124-132, XP002427518.

Payne M M et al: "Organic Field Effect Transistors from Solution Deposited Functionalized Acenes with Mobilities as High as 1 cm2/C.s" Journal of the American Chemical Society, American Chemical Society, Washington, D.C., US, col. 127, No. 14, Mar. 19, 2005, pp. 4986-4987, XP008066061 ISSN:0002-7863.

Laquindanum J G et al: "Synthesis, Morphology and Field-Effect Mobility of Anthradithiophenes" Journal of the American Chemical Society, American Chemical Society, Washington, D.C., US, vol. 120, Jan. 16, 1998, pp. 664-672, XP001152952 ISSN: 0002-7863.

Patent Abstract of Japan—Publication No. 05055568 A—"Thin Organic Film Transistor", Asahi Chem Ind Co Ltd.

J.S. Brooks, "Electronic and optical properties of functionalized pentacene compounds in the solid state", Current Applied Physics 1 (2001)301-306.

(Continued)

*Primary Examiner* — Peter O Sullivan
(74) *Attorney, Agent, or Firm* — Millen, White, Zelano & Branigan, P.C.

(57) ABSTRACT

An organic semiconducting layer formulation containing an organic binder which has a permittivity, ∈, at 1,000 Hz of 3.3 or less and a polyacene compound of Formula A:

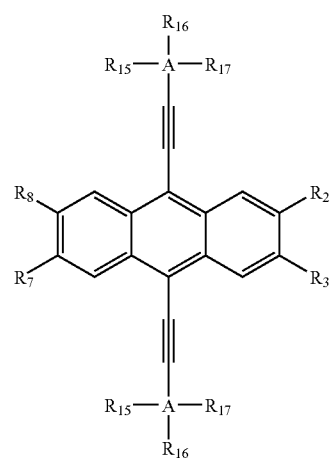

Formula 9 and processes for the preparation thereof and uses thereof in various electronic devices.

42 Claims, 1 Drawing Sheet

OTHER PUBLICATIONS

Translation of JP Application 2001-242808, Application Date: Aug. 9, 2001, Application No. P 2001-242808—"Organic Semiconductor Solution, Organic Semiconductor Thin Film, and Organic Semiconductor Element", Takashi Minakata, pp. 1-14.

Marcia M. Payne, "Stable, Crystalline Acenedithiophenes with up to Seven Linearly Fused Rings", Organic Letters 2004, vol. 6, No. 19—3325-3328.

D.R. Maulding et al., "Electronic Absorption and Fluorescence of Phenylethynyl-Substituted Acenes", The Journal of Organic Chemistry, vol. 34, No. 6, Jun. 1969, pp. 1734-1736.

Minakata, Takashi, HCAPLUS Copyright 2007 ACS on STN, 2003:154660 Organic semiconductor components with pentacene-coated transistor films.

Ohe et al. "Solution-processed organic thin-fillm transistors with vertical nanophase separation," Applied Physics Letters; 93, 0533033, Aug. 6, 2008.

Newsome et al. "Solution Processed Thin Film Transistors Incorporating a Soluble Pentacene Semicoductor," FLX1-4; Cambridge Display Technology Ltd., pp. 1465-1468.

Kang et al. "Structure and Properties of Small Molecule-Polymer Blend Semiconductors for Organic Thin Film Transistors," J. Am. Chem. Soc.; vol. 130, pp. 12273-12275, Jun. 4, 2008.

Ogier, Simon, Observations on EP1,687,830 Application No. 04819715.6; Date stamped at the USPTO Feb. 16, 2009.

Communication Persuant to Article 94(3) EPC.

* cited by examiner

ORGANIC SEMICONDUCTING LAYERS

This application is a continuation of U.S. patent application Ser. No. 10/580,552 filed May 26, 2006 now U.S. Pat. No. 7,842,942.

The present invention relates to an organic semiconducting layer formulation, a layer comprising the same, a process for preparing the formulation and layer and electronic devices (including organic field effect transistors (OFETs)) comprising the same.

In recent years, there has been development of organic semiconducting materials in order to produce more versatile, lower cost electronic devices. Such materials find application in a wide range of devices or apparatus, including organic field effect transistors (OFETs), organic light emitting diodes (OLEDs), photodetectors, photovoltaic (PV) cells, sensors, memory elements and logic circuits to name just a few. The organic semiconducting materials are typically present in the electronic device in the form of a thin layer, for example less than 1 micron thick.

Pentacene has shown promise as an organic semiconducting material. Pentacene has been described as requiring a highly crystalline structure in order to provide a molecular orientation which results in good charge mobility. Thus, in the prior art, thin films of pentacene have been vapour deposited, due in part to the fact that pentacene is rather insoluble in common solvents. However, vapour deposition requires expensive and sophisticated equipment. In view of the latter problem, one approach has been to apply a solution containing a precursor pentacene and then chemically converting, for example by heat, the precursor compound into pentacene. However, the latter method is also complex and it is difficult to control in order to obtain the necessary ordered structure for good charge mobility.

Soluble pentacene compounds have recently been described in the prior art as organic semiconducting compounds, see for example US 2003/0115755 A (Takahashi) and U.S. Pat. No. 6,690,029 (Anthony). The use of pentacenes in FETs has been suggested in WO 03/016599 (Asahi), in which a solution of a soluble pentacene was deposited on a substrate and the solvent evaporated to form a thin film of the pentacene. However, soluble pentacenes have been described in U.S. Pat. No. 6,690,029 and WO 03/016599 as still requiring a highly crystalline structure in the thin film for acceptable charge mobility, especially when used in FETs, which means that the pentacenes must still be deposited in a controlled way. Thus, the prior art is careful not to dilute the pentacene in any way, otherwise it would be expected to disrupt the crystalline structure of the pentacene and hence reduce charge mobility.

Improved charge mobility is one goal of new electronic devices. Another goal is improved stability and integrity of the organic semiconductor layer. A way potentially to improve organic semiconductor layer stability and integrity in devices would be to include the organic semiconducting component in an organic binder. However, whenever an organic semiconducting component is combined with a binder it is effectively "diluted" by the binder and a reduction of charge mobility is to be expected. Among other things, diluting an organic semiconductor by mixing with binders disrupts the molecular order in the semiconducting layer. Diluting an organic semiconducting component in the channel of an FET for example is particularly problematic as any disruption of the orbital overlap between molecules in the immediate vicinity of the gate insulator (the first few molecular layers) is expected to reduce mobility. Electrons or holes are then forced to extend their path into the bulk of the organic semiconductor, which is undesirable. Certain organic semiconducting materials are expected to be more susceptible than others to the effects of use in a binder. Since pentacenes have been taught as requiring highly ordered structures for useful charge mobility, it has not previously been considered desirable to include pentacenes with binders. In WO 03/030278 (Philips) it was attempted to use binders but there it was shown that a gradual reduction of FET mobility occurs when a (precursor) pentacene is mixed with increasing amounts of binder, even with amounts of less than 5% binder.

Certain low polarity binder resins are described in WO 02/45184 (Avecia) for use with organic semiconductors in FETs. However, a reduction in charge mobility is still expected when the semiconductor is diluted in the binder.

Among the objects of the present invention is the aim to reduce or overcome the disadvantages in organic semiconducting layers as described above.

According to a first aspect of the present invention there is provided an organic semiconducting layer formulation, which layer formulation comprises an organic binder which has a permittivity, $\epsilon$, at 1,000 Hz of 3.3 or less; and a polyacene compound of Formula A:

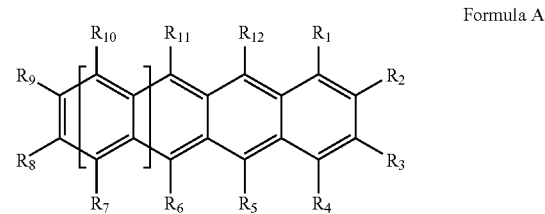

Formula A wherein each of $R_1$, $R_2$, $R_3$, $R_4$, $R_5$, $R_6$, $R_7$, $R_8$, $R_9$, $R_{10}$, $R_{11}$ and $R_{12}$, which may be the same or different, independently represents hydrogen; an optionally substituted $C_1$-$C_{40}$ carbyl or hydrocarbyl group; an optionally substituted $C_1$-$C_{40}$ alkoxy group; an optionally substituted $C_6$-$C_{40}$ aryloxy group; an optionally substituted $C_7$-$C_{40}$ alkylaryloxy group; an optionally substituted $C_2$-$C_{40}$ alkoxycarbonyl group; an optionally substituted $C_7$-$C_{40}$ aryloxycarbonyl group; a cyano group (—CN); a carbamoyl group (—C(=O)NH$_2$); a haloformyl group (—C(=O)—X, wherein X represents a halogen atom); a formyl group (—C(=O)—H); an isocyano group; an isocyanate group; a thiocyanate group or a thioisocyanate group; an optionally substituted amino group; a hydroxy group; a nitro group; a $CF_3$ group; a halo group (Cl, Br, F); or an optionally substituted silyl group; and wherein independently each pair of $R_2$ and $R_3$ and/or $R_8$ and $R_9$, may be cross-bridged to form a $C_4$-$C_{40}$ saturated or unsaturated ring, which saturated or unsaturated ring may be intervened by an oxygen atom, a sulphur atom or a group shown by formula —N($R_a$)— (wherein $R_a$ is a hydrogen atom or an optionally substituted hydrocarbon group), or may optionally be substituted; and wherein one or more of the carbon atoms of the polyacene skeleton may optionally be substituted by a heteroatom selected from N, P, As, O, S, Se and Te; and wherein independently any two or more of the substituents $R_1$-$R_{12}$ which are located on adjacent ring positions of the polyacene may, together, optionally constitute a further $C_4$-$C_{40}$ saturated or unsaturated ring optionally interrupted by O, S or —N($R_a$) where $R_a$ is as defined above) or an aromatic ring system, fused to the polyacene; and wherein n is 0, 1, 2, 3 or 4 preferably n is 0, 1 or 2, most preferably n is 0 or 2 that is the polyacene compound is a pentacene compound (n=2) or a 'pseudo pentacene' (n=0) compound.

More preferably, the pentacene compound is a compound selected from any one of Compound Groups 1 to 9 or isomers thereof wherein:

Compound Group 1 is Represented by Formula 1:

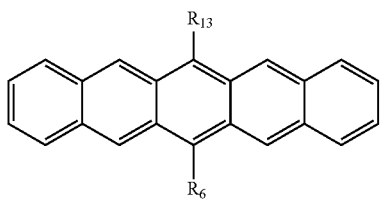

Formula 1

Compound Group 2 is Represented by Formula 2:

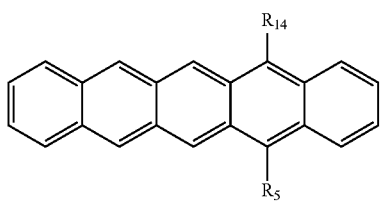

Formula 2

Compound Group 3 is Represented by Formula 3:

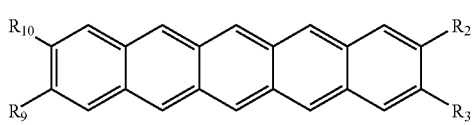

Formula 3

Compound Group 4 is Represented by Formula 4:

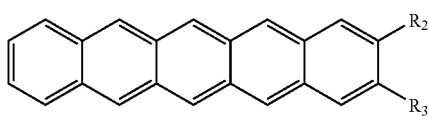

Formula 4

Compound Group 5 is Represented by Formula 5:

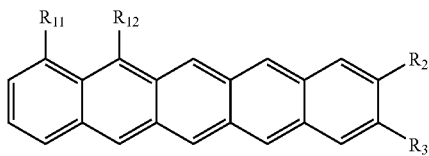

Formula 5

Compound Group 6 is Represented by Formula 6:

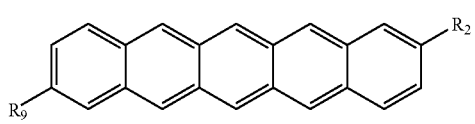

Formula 6

Compound Group 7 is Represented by Formula 7:

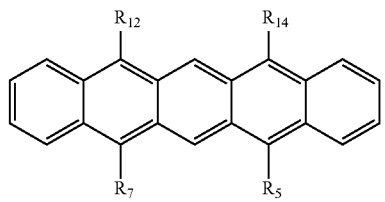

Formula 7

Compound Group 8 is Represented by Formula 8:

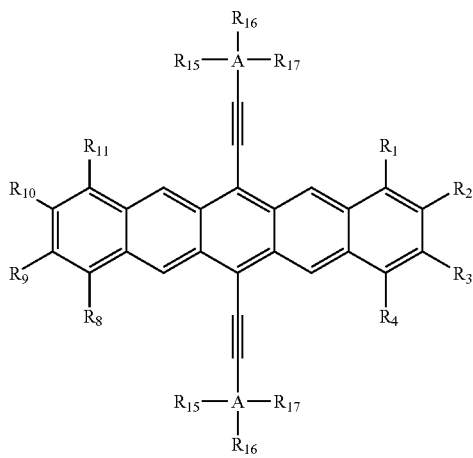

Formula 8

Compound Group 9 is Represented by the Formula 9:

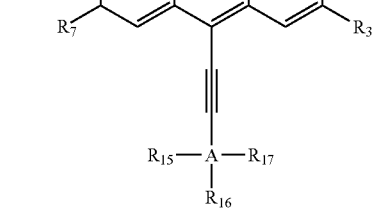

Formula 9 and wherein, in the case of Compound Group 1 $R_8$ and $R_{13}$, in the case of Compound Group 2 $R_5$ and $R_{14}$, in the case of Compound Group 3 $R_2$, $R_3$, $R_9$ and $R_{10}$, in the case of Compound Group 4 $R_2$ and $R_3$, in the case of Compound Group 5 $R_2$, $R_3$, $R_{11}$ and $R_{12}$, in the case of Compound Group 6 $R_2$ and $R_9$, in the case of Compound Group 7 $R_5$, $R_7$, $R_{12}$ and $R_{14}$, in case of Group 8 $R_1$, $R_2$, $R_3$, $R_4$, $R_8$, $R_9$, $R_{10}$, $R_{11}$, $R_{15}$, $R_{16}$, $R_{17}$ and $R_{18}$, and in the case of Group 9 $R_2$, $R_3$, $R_7$, $R_8$, $R_{15}$, $R_{16}$, $R_{17}$, each independently may be the same or different and each independently represents: H; an optionally substituted $C_1$-$C_{40}$ carbyl or hydrocarbyl group; an optionally substituted $C_1$-$C_{40}$ alkoxy group; an optionally substituted $C_8$-$C_{40}$ aryloxy group; an optionally substituted $C_7$-$C_{40}$ alkylaryloxy group; an optionally substituted $C_2$-$C_{40}$ alkoxycarbonyl group; an optionally substituted $C_7$-$C_{40}$ aryloxycarbonyl group; a cyano group (—CN); a carbamoyl group (—C(=O)NH$_2$); a haloformyl group (—C(=O)—X, wherein X represents a halogen atom); a formyl group (—C(=O)—H); an isocyano group; an isocyanate group; a thiocyanate group or a thioisocyanate group; an optionally substituted amino group; a hydroxy group; a nitro group; a CF$_3$ group; a halo group (Cl, Br, F); or an optionally substituted silyl group; and wherein independently each pair of $R_1$ and $R_2$, $R_2$ and $R_3$, $R_3$ and $R_4$, $R_8$ and $R_9$, $R_9$ and $R_{10}$, $R_{10}$ and $R_{11}$, $R_{15}$ and $R_{16}$ and $R_{16}$ and $R_{17}$ may be cross-bridged with each other to form a $C_4$-$C_{40}$ saturated or unsaturated ring, which saturated or unsaturated ring may be intervened by an oxygen atom, a sulphur atom or a group shown by formula: —N(R$_a$)— (wherein R$_a$ is a hydrogen atom or a hydrocarbon group), or may optionally be substituted; and wherein A represents Silicon or Germanium.

The "R" substituents (that is $R_1$, $R_2$ etc) in Compound Groups 1-9 denote the substituents at the positions of pentacene according to conventional nomenclature:

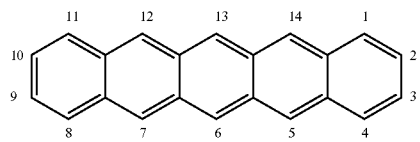

Surprisingly and beneficially, it has now been found in accordance with the present invention that combining specified soluble polyacene compounds, especially pentacene compounds from Compound Groups 1-9, (hereinafter often referred to as "the polyacene") with an organic binder resin (hereinafter sometimes simply called a "binder") results in little or no reduction in charge mobility of the polyacene, even an increase in some instances. For instance, the soluble polyacene may be dissolved in a binder resin (for example poly(α-methylstyrene) and deposited (for example by spin coating), to form an organic semiconducting layer yielding a high charge mobility, of for example 0.5-1.5 cm$^2$V$^{-1}$s$^{-1}$. This result is particularly unexpected given that the prior art teaches that in order to achieve such high mobilities a polyacene compound is expected to require strong molecular ordering. In FETs dilution in a binder would be expected to yield at least an order of magnitude reduction in mobility. It has also now been found that surprisingly even at a 1:1 ratio of binder:polyacene the mobility is comparable to that of a pure polyacene compound used alone. The results produced by the present invention are therefore surprising for both a) maintaining the mobility despite potential disruption of molecular order, and b) maintaining mobility despite the expected increase of intermolecular distance. At the same time, a semiconducting layer formed therefrom exhibits excellent film forming characteristics and is particularly stable.

In a preferred embodiment of the present invention there is provided an organic semiconducting layer formulation for use in an organic field effect transistor comprising a compound selected from Compound groups 1 to 9 more preferably groups 1 and 8;
    a binder; and
    optionally a solvent.

In an especially preferred embodiment of the present invention there is provided an organic semiconducting layer formulation for use in an organic field effect transistor comprising a compound of Formula 1;
    a binder; and
    a solvent, Formula 1

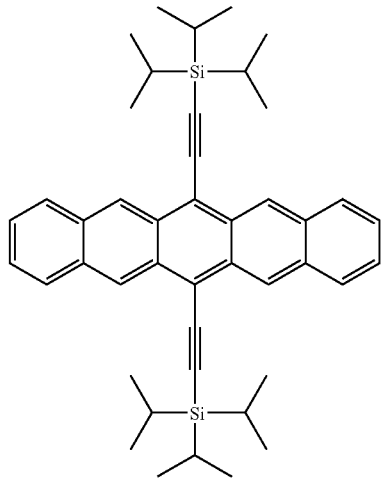

wherein the binder is selected from poly(α-methylstyrene), Topas™ 8007, poly(4-methylstyrene), polystyrene and polystyrene-co-α-methylstyrene, most preferably poly(α-methylstyrene); and the solvent is selected from toluene, ethylcyclohexane, anisole and p-xylene; most preferably toluene.

In a further especially preferred embodiment of the present invention there is provided an organic semiconducting layer formulation for use in an organic field effect transistor comprising a compound of Formula 2;
    a binder; and
    a solvent, Formula 2

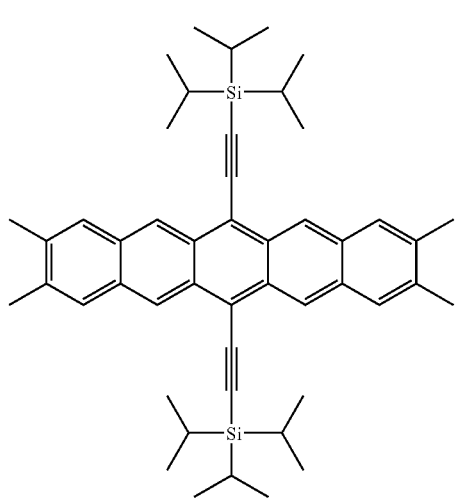

wherein the binder is selected from poly(α-methylstyrene), polyvinylcinnamate, and poly(4-vinylbiphenyl), most preferably poly(α-methylstyrene); and the solvent is 1,2-dichlorobenzene.

In yet a further especially preferred embodiment of the present invention there is provided an organic semiconducting layer formulation for use in an organic field effect transistor comprising a compound of Formula 3;
a binder; and
a solvent, Formula (3)

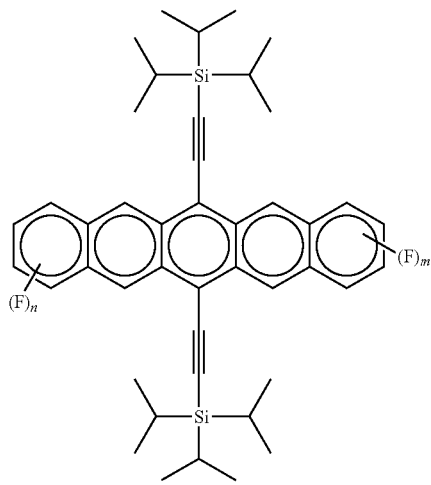

wherein
n and m is each independently 0, 1, 2, 3 or 4, more preferably 0, 1 or 2;
the binder is poly(α-methylstyrene); and
the solvent is toluene.

Once an organic semiconducting layer formulation of high mobility is obtained by combining a polyacene with a binder, the resulting formulation leads to several other advantages. For example, since the polyacenes are soluble they may be deposited in a liquid form, for example from solution. With the additional use of the binder it has now been found that the formulation may be coated onto a large area in a highly uniform manner. Without the use of binders the polyacene cannot be spin coated onto large areas as it does not result in uniform films. In the prior art, spin and drop-casting of a pure polyacene layer may in some cases result in relatively high mobility but it is difficult to provide a large area film with a constant mobility over the entire substrate which is a specific requirement for electronic devices. Furthermore, when a binder is used in the formulation it is possible to control the properties of the formulation to adjust to printing processes, for example viscosity, solid content, surface tension. Whilst not wishing to be bound by any particular theory it is also anticipated that the use of a binder in the formulation fills in volume between crystalline grains otherwise being void, making the organic semiconducting layer less sensitive to air and moisture. For example, layers formed according to the first aspect of the present invention show very good stability in OFET devices in air.

The invention also provides an organic semiconducting layer which comprises the organic semiconducting layer formulation.

The invention further provides a process for preparing the organic semiconducting layer which comprises:
(i) depositing on a substrate a liquid layer of a mixture which comprises a polyacene compound as previously described herein; and an organic binder resin or precursor thereof; and optionally a solvent; and
(ii) forming from the liquid layer a solid layer which is the organic semiconducting layer. The process is described in more detail below.

The invention additionally provides an electronic device comprising the said organic semiconducting layer. The electronic device may include, without limitation, an organic field effect transistor (OFET), organic light emitting diode (OLED), photodetector, sensor, logic circuit, memory element, capacitor or photovoltaic (PV) cell. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein. Certain polyacene compounds have been described in US 2003/0116755 A and U.S. Pat. No. 6,690,029 and the methods disclosed therein for synthesising polyacenes may be employed in the present invention in order to make the polyacene compounds described herein. Methods for making polyacenes are also described in U.S. Pat. No. 3,557,233 (American Cyanamid). Alternative, methods within the skill and knowledge of persons skilled in the art which may be used to synthesize polyacene compounds in accordance with the present invention are disclosed in Organic Letters 2004, Volume 6, number 10, pages 1609-1612.

Compound Groups 1-9 are now described in more detail.
Compound Group 1
Compound Group 1 is Represented by Formula 1:

Formula 1

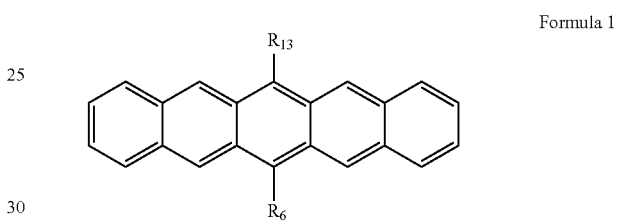

In pentacene derivatives of Compound Group 1, $R_6$ and $R_{13}$ are each independently the same or different and each independently comprise optionally substituted $C_1$-$C_{40}$ carbyl or hydrocarbyl groups. More preferably, the groups $R_6$ and $R_{13}$ comprise optionally substituted optionally unsaturated $C_1$-$C_{40}$ carbyl or hydrocarbyl groups, for example optionally substituted alkenyl, alkynyl, aryl etc. groups (optionally substituted alkynyl is a preferred group, especially optionally substituted ethynyl). Preferably, the $R_6$ and $R_{13}$ substituents are π-conjugated with the pentacene ring structure. It is most preferred however that groups $R_6$ and $R_{13}$ comprise the same substituent as each other. In the pentacene derivatives of Compound Group 1 it is preferred that none of the ring positions on the pentacene other than the 6 and 13 positions are substituted, that is they are occupied by hydrogen.

Examples of Compound Group 1 are given below:

Group 1, example 1

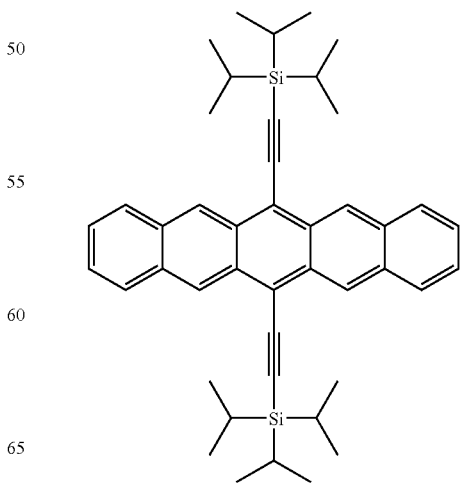

-continued

Group 1, example 2

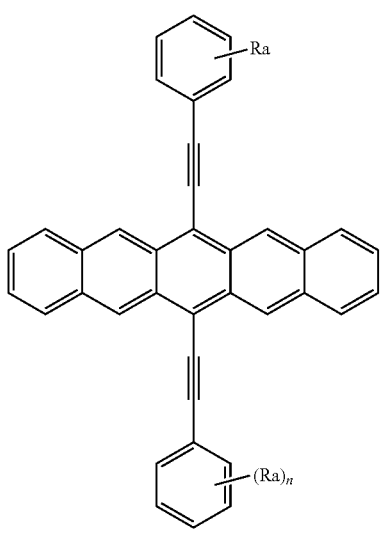

Group 1, example 3

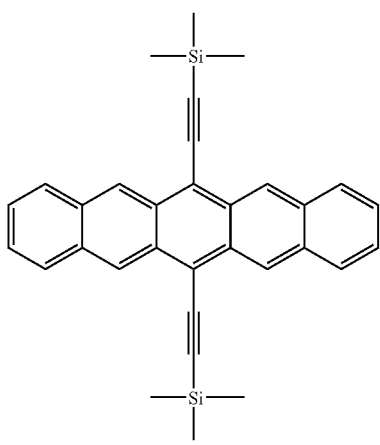

wherein Ra comprises an optionally substituted $C_{1-40}$-carbyl or hydrocarbyl group, more preferably an optionally substituted $C_{1-10}$-alkyl group; and n is 0, 1, 2, 3, 4 or 5, most preferably 1, 2 or 3.

Compound Group 2

Compound Group 2 is Represented by Formula 2:

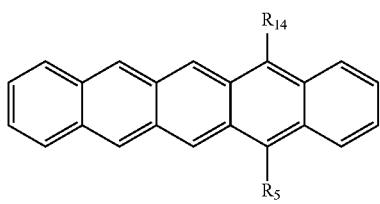

Formula 2

In pentacene derivatives of Compound Group 2, $R_5$ and $R_{14}$ are each independently the same or different and each independently comprise optionally substituted $C_1$-$C_{40}$ carbyl or hydrocarbyl groups. More preferably, the groups $R_5$ and $R_{14}$ comprise optionally substituted unsaturated $C_1$-$C_{40}$ carbyl or hydrocarbyl groups, for example optionally substituted alkenyl, alkynyl, aryl, aralkyl groups (optionally substituted alkynyl is a preferred group, especially optionally substituted ethynyl). Preferably, the $R_5$ and $R_{14}$ substituents are π-conjugated with the pentacene ring structure. It is most preferred however that $R_5$ and $R_{14}$ comprise the same substituent as each other. In pentacene derivatives of Compound Group 2 one or more of the ring positions on the pentacene derivatives other than the 5 and 14 positions may be substituted but preferably they are unsubstituted, that is they are occupied by hydrogen.

Compound Group 3

Compound Group 3 is Represented by Formula 3:

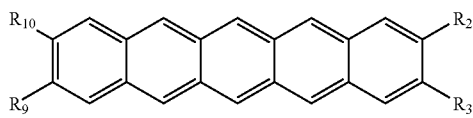

Formula 3

In pentacene derivatives of Compound Group 3, $R_2$, $R_3$, $R_9$ and $R_{10}$ are each independently the same or different and each independently comprise optionally substituted $C_1$-$C_{40}$ carbyl or hydrocarbyl groups. Further preferably, the groups $R_2$, $R_3$, $R_9$ and $R_{10}$ comprise optionally substituted $C_1$-$C_{10}$ carbyl or hydrocarbyl groups (especially alkyl), for example methyl, ethyl, propyl, butyl, pentyl, etc. One or more of the ring positions on the pentacene other than the 2, 3, 9 and 10 positions may be substituted but preferably they are unsubstituted, that is they are occupied by hydrogen. Preferably, however $R_2$ and $R_3$ are the same substituent as each other and $R_9$ and $R_{10}$ are preferably the same substituents as each other. Most preferably $R_2$, $R_3$, $R_9$ and $R_{10}$ are the same as each other.

An example of Compound Group 3 is given below:

Group 3, example

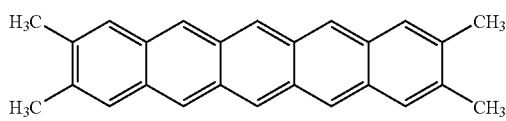

Compound Group 4

Compound Group 4 is Represented by Formula 4:

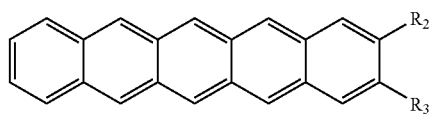

Formula 4

In pentacene derivatives of Compound Group 4, $R_2$ and $R_3$ are each independently the same or different, however, $R_2$ and $R_3$ are preferably the same substituent as each other. Preferably, the groups $R_2$ and $R_3$ comprise optionally substituted $C_1$-$C_{40}$ carbyl or hydrocarbyl groups or halo. In pentacene derivatives of Compound Group 4, one or more of the ring positions on the pentacene other than the 2 and 3 positions may be substituted but preferably they are unsubstituted, that is they are occupied by hydrogen.

An example of Compound Group 4 is given below:

Group 4 example

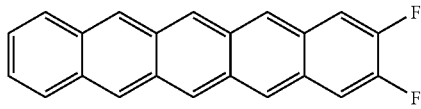

Compound Group 5
Compound Group 5 is Represented by Formula 5:

Formula 5

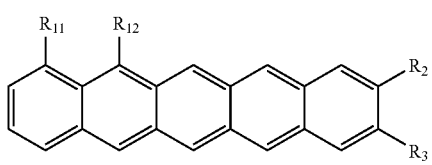

In pentacene derivatives of Compound Group 5, $R_2$, $R_3$, $R_{11}$ and $R_{12}$ are each independently the same or different. However, $R_2$ and $R_3$ are preferably the same substituent as each other, and $R_{11}$ and $R_{12}$ are preferably the same substituent as each other. Preferably, $R_2$, $R_3$, $R_{11}$ and $R_{12}$ are all the same substituent as each other. Preferably, the groups $R_2$, $R_3$, $R_{11}$ and $R_{12}$ comprise optionally substituted $C_1$-$C_{40}$ carbyl or hydrocarbyl groups. Further preferably, the groups $R_2$, $R_3$, and $R_{12}$ comprise optionally substituted $C_1$-$C_{10}$ carbyl or hydrocarbyl groups, for example methyl, ethyl, propyl, butyl, pentyl, etc. In pentacene derivatives of Compound Group 5, one or more of the ring positions on the pentacene derivative other than the 2, 3, 11 and 12 positions may be substituted but preferably, they are unsubstituted, that is they are occupied by hydrogen. An example of Compound Group 5 is given below:

Group 5, example

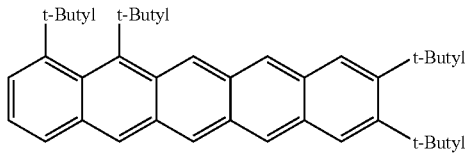

Compound Group 6
Compound Group 6 is Represented by Formula 6:

Formula 6

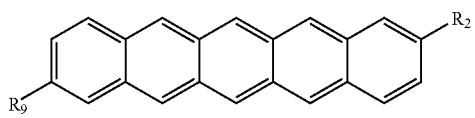

In pentacene derivatives of Compound Group 6, $R_2$ and $R_9$ are each independently the same or different. However, $R_2$ and $R_3$ are preferably the same substituent as each other. Preferably, the groups $R_2$ and $R_9$ comprise optionally substituted $C_1$-$C_{40}$ carbyl or hydrocarbyl groups. In the pentacene derivatives of Compound Group 6, one or more of the ring positions on the pentacene other than the 2 and 9 positions may be substituted but preferably they are unsubstituted, that is they are occupied by hydrogen.

An example of a Compound of Group 6 is given below:

Group 6 example

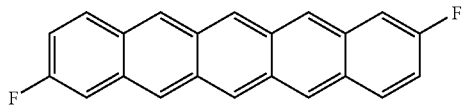

Compound Group 7
Compound Group 7 is Represented by Formula 7:

Formula 7

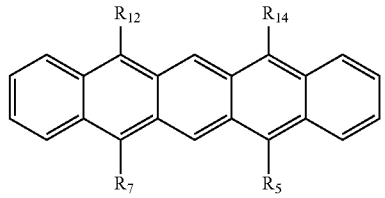

In pentacene derivatives of Compound Group 7, $R_5$, $R_7$, $R_{12}$ and $R_{14}$ are each independently the same or different. However it is preferred that $R_5$ and $R_{14}$ are the same substituent as each other, and that $R_7$ and $R_{12}$ are the same substituent as each other. More preferably, $R_5$, $R_{14}$, $R_7$ and $R_{12}$ are all the same substituent as each other. Preferably, the groups $R_5$, $R_{14}$, $R_7$ and $R_{12}$ comprise optionally substituted $C_1$-$C_{40}$ carbyl or hydrocarbyl groups. In the pentacene derivatives of Compound Group 7, one or more of the ring positions on the pentacene other than the 5, 14, 7 and 12 positions may be substituted but preferably they are unsubstituted, that is they are occupied by hydrogen.

An example of a Compound of Group 7 is given below:

Group 7 example

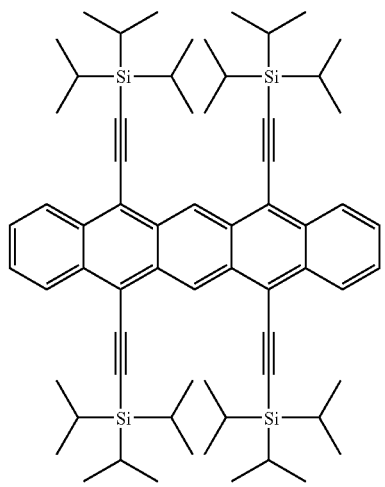

Compound Group 8
Compound Group 8 is Represented by Formula 8:

Formula 8

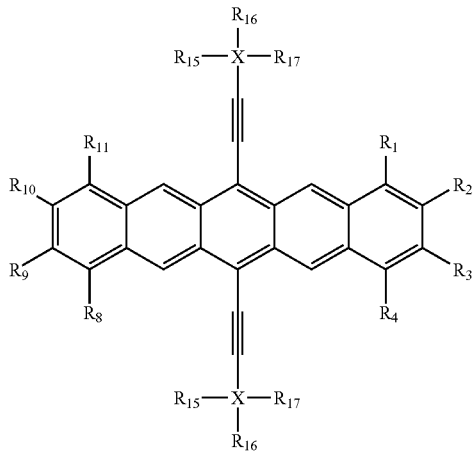

In pentacene derivatives of Compound Group 8 and isomers thereof, $R_1$, $R_2$, $R_3$, $R_4$, $R_6$, $R_9$, $R_{10}$, $R_{11}$, $R_{15}$, $R_{16}$ and $R_{17}$ are each independently the same or different. $R_1$, $R_2$, $R_3$, $R_4$, $R_8$, $R_9$, $R_{10}$ and $R_{11}$, each independently comprises H, optionally substituted $C_{1-40}$ carbyl or hydrocarbyl groups, for example optionally substituted alkenyl, alkyaryl, aryl etc groups or halo groups for example F, Cl, Br. More preferably, $R_1$, $R_2$, $R_3$, $R_4$, $R_9$, $R_9$, $R_{10}$ and $R_{17}$ comprise optionally substituted $C_{1-10}$-alkyl groups for example methyl, ethyl, propyl, butyl, pentyl etc., most preferably methyl; halogen, for example F, Cl, Br most preferably F, or $R_2$, and $R_3$ and $R_9$ and $R_{10}$ together with the carbon atoms to which they are attached form a $C_4$-$C_{40}$ saturated or unsaturated ring, more preferably an optionally substituted $C_4$-$C_{10}$ saturated or unsaturated ring, intervened by one or more oxygen or sulphur atoms or a group represented by formula —N($R_a$), wherein $R_a$ is a hydrogen atom or a hydrocarbon group. In the pentacene derivatives of Formula 8 $R_{15}$, $R_{16}$ and $R_{17}$ may each independently be the same or different, preferably $R_{15}$, $R_{16}$ and $R_{17}$ are the same and comprise an optionally substituted $C_1$-$C_{40}$ carbyl or hydrocarbyl group, for example a $C_1$-$C_{40}$ alkyl group (preferably $C_1$-$C_4$ alkyl and most preferably methyl, ethyl, n-propyl or isopropyl) which may optionally be substituted for example with a halogen atom; a $C_6$-$C_{40}$ aryl group (preferably phenyl) which may optionally be substituted for example with a halogen atom; a $C_6$-$C_{40}$ arylalkyl group which may optionally be substituted for example with a halogen atom; a $C_1$-$C_{40}$ alkoxy group which may optionally be substituted for example with a halogen atom; or a $C_6$-$C_{40}$ arylalkyloxy group which may optionally be substituted for example with a halogen atom or $R_{15}$ and $R_{16}$ or $R_{16}$ and $R_{17}$ together with for example the atom to which they are attached form a $C_4$-$C_{40}$ saturated or unsaturated ring, more preferably an optionally substituted $C_4$-$C_{10}$ saturated or unsaturated ring, intervened by one or more oxygen or sulphur atoms or a group represented by formula —N($R_a$), wherein $R_a$ is a hydrogen atom or a hydrocarbon group and/or isomers thereof. Preferably, $R_{15}$, $R_{16}$ and $R_{17}$ are each independently selected from optionally substituted $C_{1-10}$ alkyl (more preferably $C_{1-4}$ and even more preferably $C_{1-3}$ alkyl, for example isopropyl) and optionally substituted $C_{6-10}$ aryl (preferably phenyl).

In the pentacene derivatives of Formula 8, X is preferably Silicon or Germanium, most preferably silicon.

In one preferred embodiment, when X is silicon forming a silyl group, $R_{15}$, $R_{16}$ and $R_{17}$ are preferably the same group as each other, for example the same optionally substituted alkyl group, as in triisopropylsilyl. Preferably, in this embodiment, the groups $R_{15}$, $R_{16}$ and $R_{17}$ are the same optionally substituted $C_{1-10}$ (more preferably $C_{1-4}$ and even more preferably $C_{1-3}$) alkyl group. A preferred alkyl group in this case is isopropyl.

A silyl group of formula —Si($R_{15}$)($R_{16}$)($R_{17}$) as described above is a preferred optional substituent for the $C_1$-$C_{40}$ carbyl or hydrocarbyl group etc.

Additionally, in an extension to this further preferred embodiment it is preferred that when $R_2$, $R_3$, $R_9$ and $R_{10}$ are $C_{1-10}$-alkyl, one or more of $R_2$, $R_3$, $R_9$ and $R_{10}$ are preferably methyl, or one or more of $R_1$, $R_2$, $R_3$, $R_4$, $R_8$, $R_9$, $R_{10}$ and $R_{11}$ is F. In a further preferred embodiment of compound group 8, $R_1$, $R_2$, $R_3$, $R_4$, $R_8$, $R_9$, $R_{10}$ and $R_{11}$ are each H. $R_{15}$, $R_{16}$ and $R_{17}$ are $C_{1-10}$-alkyl, more preferably $C_{1-5}$-alkyl for example, methyl, ethyl or propyl.

In an additional embodiment of Group 8 any two or more of the substituents which are located on adjacent ring positions of the polyacene may, together with the adjacent ring portion to which they are attached, optionally constitute a further aromatic or heterocyclic ring system fused to the polyacene compound. An example of this type of Group 8 pentacene compound is illustrated below in Group 8, example 6, wherein each pair of adjacent substituents $R_1$ and $R_2$, $R_3$ and $R_4$, $R_9$ and $R_9$, and $R_{10}$ and $R_{11}$ constitute a benzene ring fused to the pentacene:

In the pentacene derivatives of compound Group 8 one or more of the ring positions on the pentacene derivative other than the 1, 2, 3, 4, 6, 8, 9, 10, 11 and 13 positions may be substituted, but preferably they are unsubstituted, that is, they are occupied by hydrogen.

Examples of Compound Group 8 compounds are given below wherein $R_{15}$, $R_{16}$ and $R_{17}$ and n and m are as previously described above:

Group 8, example 1

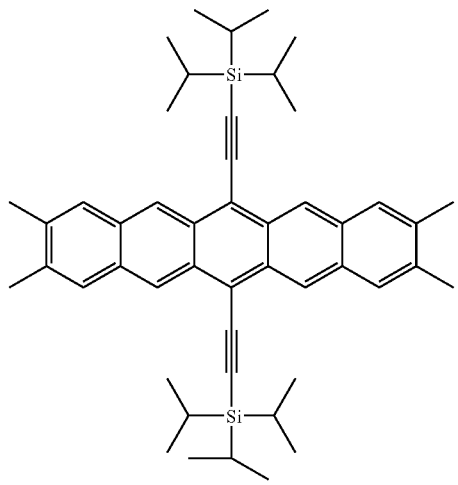

Group 8, example 2

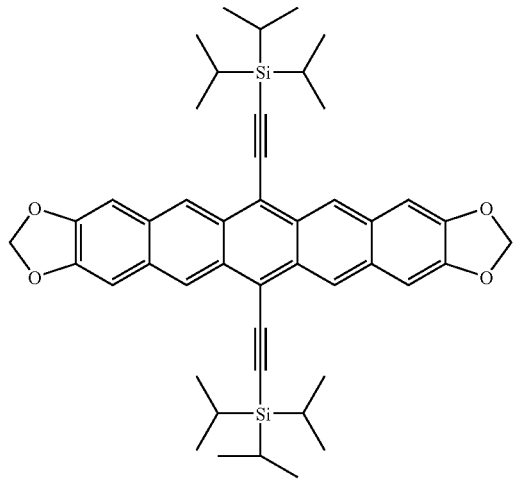

-continued

Group 8, example 3

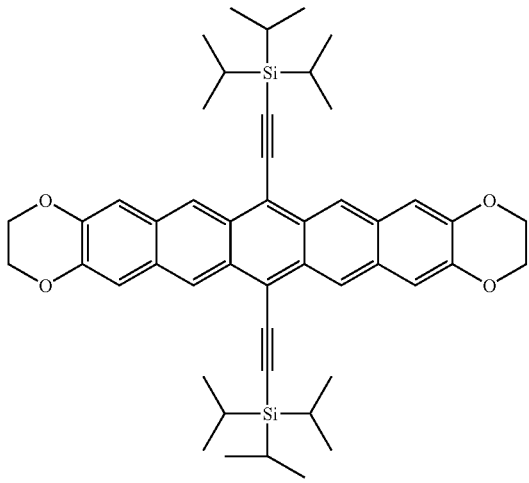

Group 8, example 4

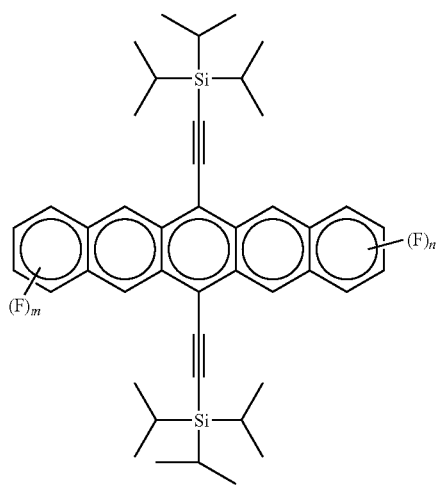

Group 8, example 5

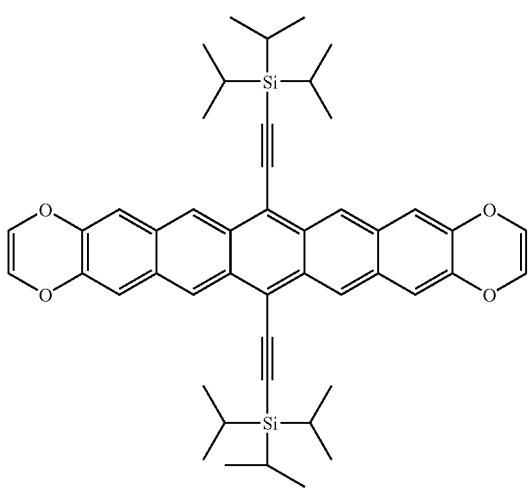

-continued

Group 8, example 6

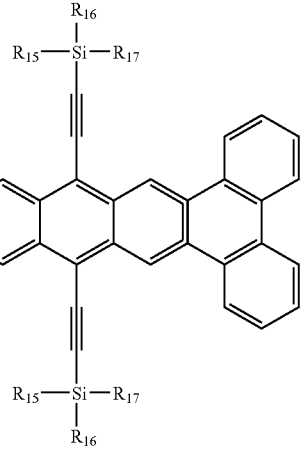

Compound Group 9

Compound Group 9 is Represented by Formula 9:

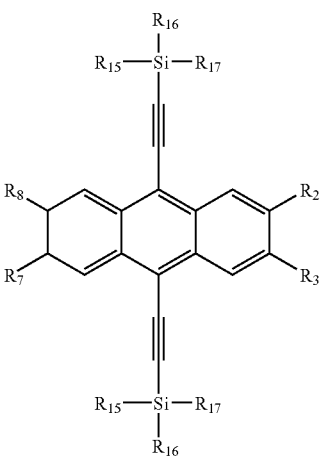

Formula 9

In the pentacene derivatives of Compound Group 9, $R_2$, $R_3$, $R_7$, $R_8$, $R_{15}$, $R_{16}$ and $R_{17}$ are each independently the same or different and each independently comprise H, or optionally substituted $C_1$-$C_{40}$-carbyl or hydrocarbyl groups. $R_2$ and $R_3$ may be the same or different but are preferably the same substituent as each other. $R_7$ and $R_8$ may also be the same or different but are preferably the same substituent as each other. Preferably $R_2$, $R_3$, $R_7$ and $R_8$ are the same substituent as each other. Most preferably $R_2$ and $R_3$ and $R_7$ and $R_8$ together with the carbon atom to which they are attached form a $C_4$-$C_{40}$ saturated or unsaturated ring, more preferably a $C_4$-$C_{10}$ saturated or unsaturated ring intervened by one or more oxygen or sulphur atoms or a group represented by the formula —N($R_a$) wherein $R_a$ is a hydrogen atom or a hydrocarbon group, thereby forming a pseudo-pentacene compound. Preferred pseudo-pentacene derivatives of Compound Group 9 are as shown in Formula 9a and Formula 9b and isomers thereof, wherein one or more of the carbon atoms of the polyacene skeleton may be substituted by a heteroatom selected from N, P, As, O, S, Se and Te, preferably N or S.

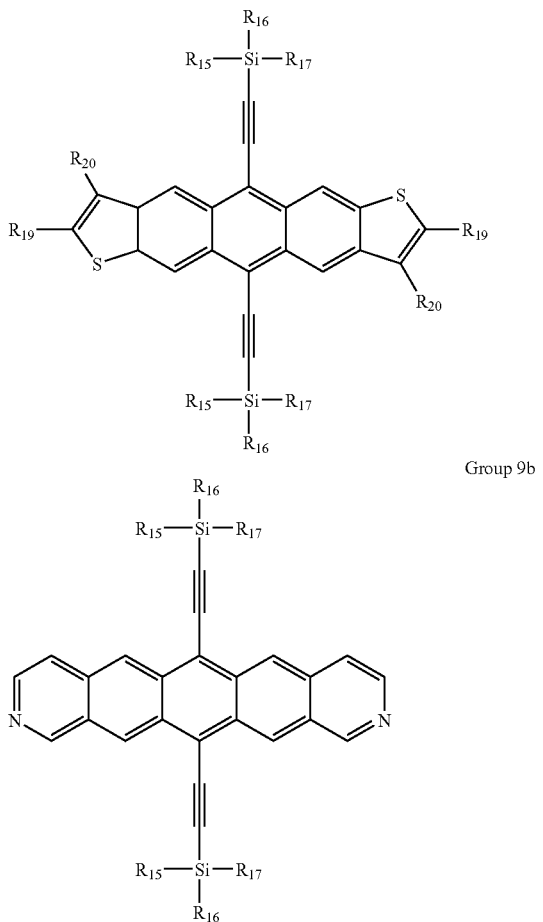

Group 9a

Group 9b

In the pseudo-pentacene derivatives of Compound Group 9 as exemplified by formula 9a $R_{19}$ and $R_{20}$ are preferably the same substituent and comprise optionally substituted $C_{1-40}$ carbyl or hydrocarbyl groups. More preferably $R_{19}$ and $R_{20}$ each independently comprise optionally substituted, optionally unsaturated $C_{1-40}$ carbyl or hydrocarbyl groups, for example, optionally substituted alkyl, alkenyl, alkynyl, aryl or aralkyl groups or $R_{19}$ and $R_{20}$ either together with the carbon atoms to which they are attached or independently in combination with a substituent on a suitably adjacent atom from an optionally substituted $C_4$-$C_{40}$ saturated or unsaturated ring optionally intervened by one or more oxygen or sulphur atoms or a group represented by Formula —N($R_a$) wherein $R_a$ is a hydrogen atom or a hydrocarbon group. Most preferably the ring (formed by $R_{19}$ and $R_{20}$ together with the carbon atoms to which they are attached) is intervened by one or more oxygen atoms. However, it is most preferred that $R_{19}$ and $R_{20}$ are the same substituent and comprise hydrogen or a saturated or unsaturated $C_{1-4}$-alkyl group for example methyl, ethyl, propyl, or butyl, most preferably $R_{19}$ and $R_{20}$ are each independently a methyl group or a hydrogen atom.

In the pseudo pentacene derivatives of compound groups 9a and 9b, $R_{15}$, $R_{16}$, $R_{17}$ may be the same or different, most preferably $R_{15}$, $R_{16}$ and $R_{17}$ are the same and are as described in relation to compounds of Formula 8 above.

In the pseudo pentacene derivatives of Compound Group 9 one or more of the ring positions on the compound may be substituted, for example in order to form additional optionally substituted rings but preferably the other ring positions are unsubstituted, that is they are occupied by hydrogen.

In the polyacenes of the present invention (especially Compound Groups 1-9), the $C_1$-$C_{40}$ carbyl or hydrocarbyl group may be a saturated or unsaturated acyclic group, or a saturated or unsaturated cyclic group. Unsaturated acyclic or cyclic groups are preferred, especially alkenyl and alkynyl groups (especially ethynyl). Where the $C_1$-$C_{40}$ carbyl or hydrocarbyl group is acyclic, the group may be linear or branched. The $C_1$-$C_{40}$ carbyl or hydrocarbyl group includes for example: a $C_1$-$C_{40}$ alkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_1$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group and a $C_4$-$C_{20}$ polyenyl group, respectively; more preferred are a $C_1$-$C_{10}$ alkyl group, a $C_2$-$C_{10}$ alkenyl group, a $C_2$-$C_{10}$ alkynyl group (especially ethynyl), a $C_3$-$C_{10}$ allyl group, a $C_4$-$C_{10}$ alkyldienyl group, a $C_6$-$C_{12}$ aryl group and a $C_4$-$C_{10}$ polyenyl group, respectively; and most preferred is $C_{2-10}$ alkynyl.

Examples of the alkyl group are, without limitation, methyl, ethyl, propyl, n-butyl, t-butyl, dodecanyl, trifluoromethyl, perfluoro-n-butyl, 2,2,2-trifluoroethyl, benzyl, 2-phenoxyethyl, etc. Examples of the alkynyl group are ethynyl and propynl. Examples of the aryl group are, without limitation, phenyl, 2-tolyl, 3-tolyl, 4-tolyl, naphthyl, biphenyl, 4-phenoxyphenyl, 4-fluorophenyl, 3-carbomethoxyphenyl, 4-carbomethoxyphenyl, etc. Examples of the alkoxy group are, without limitation, methoxy, ethoxy, 2-methoxyethoxy, t-butoxy, etc. Examples of the aryloxy group are, without limitation, phenoxy, naphthoxy, phenylphenoxy, 4-methylphenoxy, etc. Examples of the amino group are, without limitation, dimethylamino, methylamino, methylphenylamino, phenylamino, etc.

In the polyacenes of the present invention, the optional substituents on the said $C_1$-$C_{40}$ carbyl or hydrocarbyl groups for $R_1$ etc, preferably are selected from: silyl, sulpho, sulphonyl, formyl, amino, imino, nitrilo, mercapto, cyano, nitro, halo, $C_1$-$C_4$alkyl, $C_{6-12}$aryl, $C_{1-4}$ alkoxy, hydroxy and/or all chemically possible combinations thereof. More preferable among these optional substituents are silyl and $C_{6-12}$ aryl and most preferable is silyl.

The silyl group in this specification, which may be optionally substituted, may be shown by formula: —Si($R_{15}$)($R_{16}$)($R_{17}$), wherein each of $R_{15}$, $R_{16}$ and $R_{17}$, which may be the same or different, independently represents hydrogen, a $C_1$-$C_{40}$-alkyl group (preferably $C_1$-$C_4$-alkyl and most preferably methyl, ethyl, n-propyl or isopropyl) which may optionally be substituted for example with a halogen atom; a $C_6$-$C_{40}$-aryl group (preferably phenyl) which may optionally be substituted for example with a halogen atom; a $C_6$-$C_{40}$-aralalkyl group which may optionally be substituted for example with a halogen atom; a $C_1$-$C_{40}$-alkoxy group which may optionally be substituted for example with a halogen atom; or a $C_6$-$C_{40}$-arylalkyloxy group which may optionally be substituted for example with a halogen atom. Preferably, $R_{15}$, $R_{16}$ and $R_{17}$ are each independently selected from optionally substituted $C_{1-10}$-alkyl (more preferably $C_{1-4}$ and even more preferably $C_{1-3}$-alkyl, for example isopropyl) and optionally substituted $C_{6-10}$-aryl (preferably phenyl).

In one preferred embodiment of silyl group, $R_{15}$, $R_{16}$ and $R_{17}$ are preferably the same group as each other, for example the same optionally substituted alkyl group, as in triisopropylsityl. Preferably, in that preferred embodiment, the groups $R_{15}$, $R_{16}$ and $R_{17}$ are the same optionally substituted $C_{1-10}$ (more preferably $C_{1-4}$ and even more preferably $C_{1-3}$) alkyl group. A preferred alkyl group in this case is isopropyl, A silyl group of formula —Si($R_{15}$)($R_{16}$)($R_{17}$) as described above is a preferred optional substituent for the $C_1$-$C_{40}$-carbyl or hydrocarbyl group etc.

Examples of the silyl group —Si($R_{15}$)($R_{16}$)($R_{17}$) are, without limitation, trimethylsilyl, triethylsilyl, tripropylsilyl, dimethylethylsilyl, diethylmethylsilyl, dimethylpropylsilyl, dimethylisopropylsilyl, dipropylmethylsilyl, diisopropylmethylsilyl, dipropylethylsilyl, diisopropylethylsilyl, diethylisopropylsilyl, triisopropylsilyl, trimethoxysilyl, triethoxysilyl, diphenylisopropylsilyl, diisopropylphenylsilyl, diphenylethylsilyl, diethylphenylsilyl, diphenylmethylsilyl, triphenoxysilyl, dimethylmethoxysilyl, dimethylphenoxysilyl, methylmethoxyphenyl, etc. For each example in the foregoing list, the alkyl, aryl or alkoxy group may optionally be substituted.

Most preferred pentacene compounds according to the present invention are those of Compound Groups 1, 2, 8 and 9, more especially preferred are compound groups 1 and 8, Examples of compounds of Group 1 and 2 include without limitation: 6,13-bis(trimethylsilylethynyl)pentacene, 6,13-bis(triethylsilylethynyl)pentacene, 6,13-bis(tripropylsilylethynyl)pentacene, 6,13-bis(dimethylethylsilylethynyl)pentacene, 6,13-bis(diethylmethylsilylethynyl)pentacene, 6,13-bis(dimethylpropylsilylethynyl)pentacene, 6,13-bis(dimethylisopropylsilylethynyl)pentacene, 6,13-bis(dipropylmethylsilylethynyl)pentacene, 6,13-bis(diisopropylmethylsilylethynyl)pentacene, 6,13-bis(dipropylethylsilylethynyl)pentacene, 6,13-bis(diisopropylethylsilylethynyl)pentacene, 6,13-bis(diethylisopropylsilylethynyl)pentacene, 6,13-bis(triisopropylsilylethynyl)pentacene 6,13-bis(trimethoxysilylethynyl)pentacene, 6,13-bis(triethoxysilylethynyl)pentacene, 6,13-bis(triphenylsilylethynyl)pentacene, 6,13-bis(diphenylisopropylsilylethynyl)pentacene, 6,13-bis(diisopropylphenylsilylethynyl)pentacene, 6,13-bis(diphenylethylsilylethynyl)pentacene, 6,13-bis(diethylphenylsilylethynyl)pentacene, 6,13-bis(diphenylmethylsilylethynyl)pentacene, 6,13-bis(triphenoxysilylethynyl)pentacene, 6,13-bis(dimethylmethoxysilylethynyl)pentacene, 6,13-bis(dimethylphenoxysilylethynyl)pentacene, 6,13-bis(methylmethoxyphenylethynyl)pentacene, 6,13-bis(cyclopentamethylenesilane)pentacene, 6,13-bis(cyclotetramethylenesilane)pentacene, 5,14-bis(trimethylsilyiethynyl)pentacene, 5,14-bis(triethylsilylethynyl)pentacene, 5,14-bis(tripropylsilylethynyl)pentacene, 5,14-bis(dimethylethylsilylethynyl)pentacene, 5,14-bis(diethylmethylsilylethynyl)pentacene, 5,14-bis(dimethylpropylsilylethynyl)pentacene, 5,14-bis(dimethylisopropylsilylethynyl)pentacene, 5,14-bis(dipropylmethylsilylethynyl)pentacene, 5,14-bis(diisopropylmethylsilylethynyl)pentacene, 5,14-bis(dipropylethylsilylethynyl)pentacene, 5,14-bis(diisopropylethylsilylethynyl)pentacene, 5,14-bis(diethylisopropylsilylethynyl)pentacene, 5,14-bis(triisopropylsilylethynyl)pentacene, 5,14-bis(trimethoxysilylethynyl)pentacene, 5,14-bis(triethoxysilylethynyl)pentacene, 5,14-bis(triphenylsilylethynyl)pentacene, 5,14-bis(diphenylisopropylsilylethynyl)pentacene, 5,14-bis(diisopropylphenylsilylethynyl)pentacene, 5,14-bis(diphenylethylsilylethynyl)pentacene, 5,14-bis(diethylphenylsilylethynyl)pentacene, 5,14-bis(diphenylmethylsilylethynyl)pentacene, 5,14-bis(triphenoxysilylethynyl)pentacene, 5,14-bis(dimethylmethoxysilylethynyl)pentacene, 5,14-bis(dimethylphenoxysilylethynyl)pentacene, 5,14-bis(methylmethoxyphenylethynyl)pentacene.

Examples of compounds of Group 8 and 9 include without limitation: 2,3,9,10-tetramethyl-6,13-bis(triisopropylsilylethynyl)pentacene, 5,11-bis(triisopropylsilyl ethynyl)anthra[2,3-b;6,7-b']dithiophene, 5,11-bis(triisopropylsilylethynyl)anthra[2,3-b:7,6-b']dithiophene, 1,8-difluouro-6,13-bis(triisopropylsilylethynyl)pentacene, 1,11-difluoro-6,13-bis(triisopropylsilylethynyl)pentacene and 2,3,9,10-tetrafluoro-6,13-bis(triisopropylsilylethynyl)pentacene.

Preferred among Compound Groups 1 and 8 are compounds of Formula 1A, 8A or 8B, especially Formula 1A:

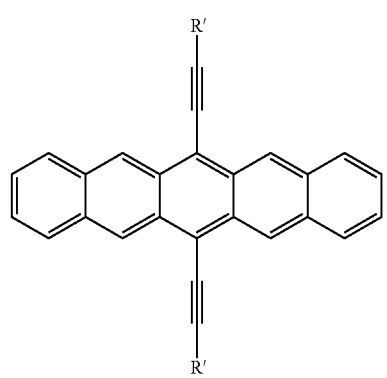

Formula 1A

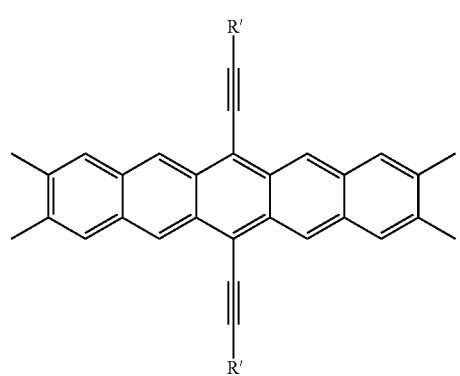

Formula 8A

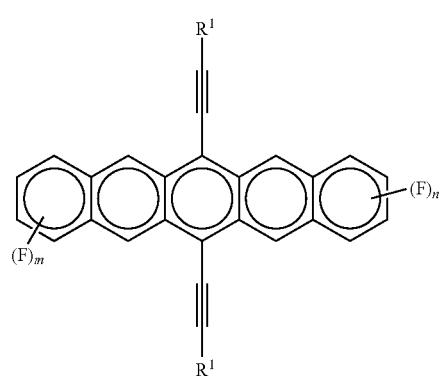

Formula 8B wherein each R' is independently selected from a $C_{2-40}$ alkyl group, a $C_{2-40}$ alkoxy group, a $C_{2-40}$ alkenyl group, $C_{2-40}$ alkynyl group, a $C_{6-18}$ aryl or heteroaryl group, $C_6$-$C_{40}$ aryloxy group, $C_7$-$C_{40}$ alkylaryloxy group, a $C_2$-$C_{40}$ alkoxycarbonyl group, a $C_7$-$C_{40}$ aryloxycarbonyl group, or a silyl group, each of which may be optionally substituted, or a cyano group (—CN), a carbamoyl group (—C(=O)NH$_2$), a haloformyl group (—C(=O)—X, wherein X represents a halogen atom), a formyl group (—C(=O)—H), an isocyano group, an isocyanate group, a thiocyanate group or a thioisocyanate group, an optionally substituted amino group, an imino group, a hydroxy group, a halo, a sulpho group, a sulphonyl group a mercapto group, or a nitro group; and m and n in Formula 8B are each independently 0, 1, 2, 3 or 4, more preferably 0, 1 or 2. Preferably, in Formulae 1A, 8A and 8B each R' is independently selected from $C_{6-18}$ aryl and silyl, which may both optionally be substituted. Preferably in Formula 1A, 8A and 8B at least one R' and most preferably both R' is silyl, wherein the silyl group is preferably defined as above, that is, a silyl group of formula —Si($R_{15}$)($R_{16}$)($R_{17}$). These latter highly preferred compounds thus have Formulae 1A', 8A' and 8B':

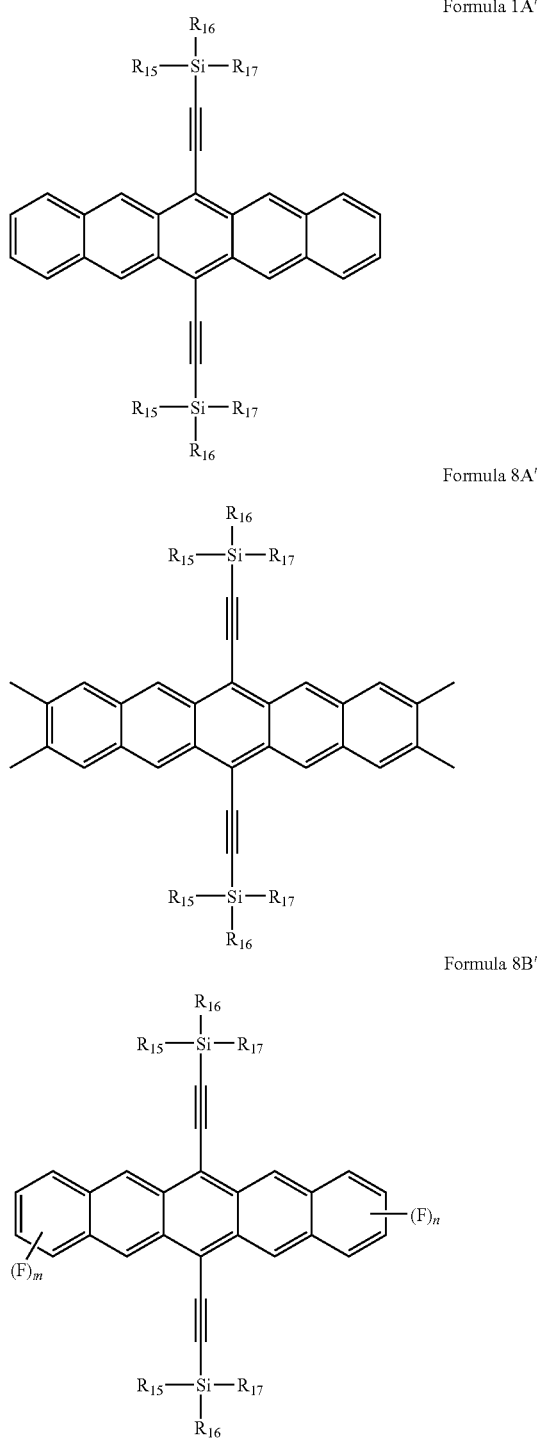

Formula 1A'

Formula 8A'

Formula 8B'

In one type of preferred embodiment, $R_{15}$, $R_{16}$ and $R_{17}$ in Formulae 1A', 8A' and 8B' are preferably the same as each other, for example the same alkyl group, as in 6,13-bis-(tri-isopropylsilylethynyl)pentacene. In this particular preferred embodiment, $R_{15}$, $R_{16}$ and $R_{17}$ are preferably the same $C_{1-10}$ (preferably $C_{1-4}$ and more preferably $C_{1-3}$) alkyl group which may optionally be substituted. Optionally substituted isopropyl is a preferred alkyl group for such embodiments.

In some cases it may be desirable to control the solubility of the polyacene in common organic solvents in order to make devices easier to fabricate. This may have advantages in making an FET for example, where solution coating, say, a dielectric onto the polyacene layer may have a tendency to dissolve the polyacene. Also, once a device is formed, a less soluble polyacene may have less tendency to "bleed" across organic layers. In one embodiment of a way to control solubility of the pentacene derivatives of Formulae 1B above, at least one of $R_{15}$, $R_{16}$ and $R_{17}$ contains an optionally substituted aryl (preferably phenyl) group. Thus, at least one of $R_{15}$, $R_{16}$ and $R_{17}$ may be an optionally substituted $C_{6-18}$ aryl (preferably phenyl) group, an optionally substituted $C_{6-18}$ aryloxy (preferably phenoxy) group, an optionally substituted $C_{6-20}$ arylalkyl (for example benzyl) group, or an optionally substituted $C_{6-20}$ arylalkyloxy (for example benzyloxy) group. In such cases, the remaining groups, if any, among $R_{15}$, $R_{16}$ and $R_{17}$ are preferably $C_{1-10}$ (more preferably $C_{1-4}$) alkyl groups which may be optionally substituted. An example of such an embodiment is given below in Formulae 1C, wherein Ar represents an aryl-containing group for example an optionally substituted $C_{6-18}$ aryl group, an optionally substituted $C_{6-18}$ aryloxy group, an optionally substituted $C_{6-20}$ arylalkyl group or an optionally substituted $C_{6-20}$ arylalkyloxy group:

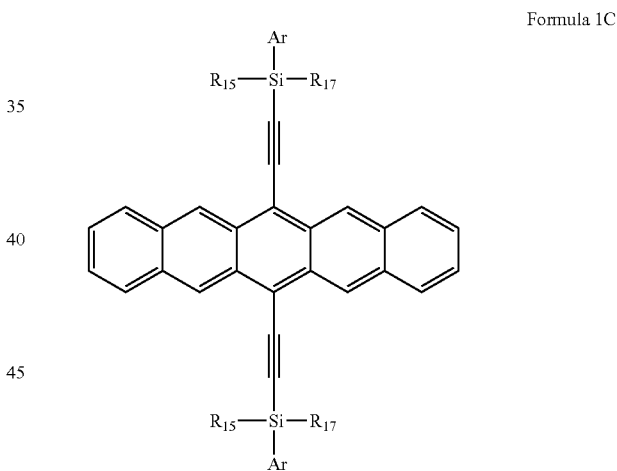

Formula 1C

In Formulae 1C, $R_{15}$ and $R_{17}$ are preferably the same group as each other, for example an isopropyl group.

Examples of compounds of Formulae 1C include, without limitation: 6,13-bis(triphenylsilylethynyl)pentacene, 6,13-bis(diphenylisopropylsilylethynyl)pentacene, 6,13-bis(diisopropylphenylsilylethynyl)pentacene, 6,13-bis(diphenylethylsilylethynyl)pentacene, 6,13-bis(diethylphenylsilylethynyl)pentacene, 6,13-bis(diphenylmethylsilylethynyl)pentacene, 6,13-bis(triphenoxysilylethynyl)pentacene, 6,13-bis(dimethylphenoxysilylethynyl)pentacene, 6,13-bis(methylmethoxyphenylethynyl)pentacene, 5,14-bis(triphenylsilylethynyl)pentacene, 5,14-bis(diphenylisopropylsilylethynyl)pentacene, 5,14-bis(diisopropylphenylsilylethynyl)pentacene, 5,14-bis-(diphenylethylsilylethynyl)pentacene, 5,14-bis(diethylphenylsilylethynyl)pentacene, 5,14-bis(diphenylmethylsilylethynyl)pentacene, 5,14-bis (triphenoxysilylethynyl)pentacene, 5,14-bis(dimethylphenoxysilylethynyl)pentacene, 5,14-bis(methylmethoxyphenylethynyl)pentacene.

Additional examples of preferred compounds of Groups 1 and 8 are as previously Illustrated under the general description of each group.

In a preferred embodiment of the present invention the semiconducting polyacene has a field effect mobility, μ, of more than $10^{-5}$ cm$^2$V$^{-1}$s$^{-1}$, preferably of more than $10^{-4}$ cm$^2$V$^{-1}$s$^{-1}$, more preferably of more than $10^{-3}$ cm$^2$V$^{-1}$s$^{-1}$, still more preferably of more than $10^{-2}$ cm$^2$V$^{-1}$s$^{-1}$ and most preferably of more than $10^{-1}$ cm$^2$V$^{-1}$s$^{-1}$.

The binder, which is a polymer, may comprise either an insulating binder or a semiconducting binder, or mixtures thereof may be referred to herein as the organic binder, the polymeric binder or simply the binder.

Preferred binders according to the present invention are materials of low permittivity, that is, those having a permittivity, ∈ at 1,000 Hz of 3.3 or less. The organic binder preferably has a permittivity at 1,000 Hz of less than 3.0, more preferably 2.9 or less. Preferably the organic binder has a permittivity at 1,000 Hz of greater than 1.7. It is especially preferred that the permittivity of the binder is in the range from 2.0 to 2.9. Whilst not wishing to be bound by any particular theory it is believed that the use of binders with a permittivity of greater than 3.3 at 1,000 Hz, may lead to a reduction in the OSC layer mobility in an electronic device, for example an OFET. In addition, high permittivity binders could also result in increased current hysteresis of the device, which is undesirable.

An example of a suitable organic binder is polystyrene. Further examples are given below.

In one type of preferred embodiment, the organic binder is one in which at least 95%, more preferably at least 98% and especially, all of the atoms consist of hydrogen, fluorine and carbon atoms.

It is preferred that the binder normally contains conjugated bonds especially conjugated double bonds and/or aromatic rings.

The binder should preferably be capable of forming a film, more preferably a flexible film. Polymers of styrene and alpha-methyl styrene, for example copolymers including styrene, alpha-methylstyrene and butadiene may suitably be used.

Binders of low permittivity of use in the present invention have few permanent dipoles which could otherwise lead to random fluctuations in molecular site energies. The permittivity (dielectric constant) can be determined by the ASTM D150 test method.

It is also preferred that in the present invention binders are used which have solubility parameters with low polar and hydrogen bonding contributions as materials of this type have low permanent dipoles. A preferred range for the solubility parameters of a binder for use in accordance with the present invention is provide in Table 1 below.

TABLE 1

| | Hansen parameter | | |
|---|---|---|---|
| | $\delta_d$ MPa$^{1/2}$ | $\delta_p$ MPa$^{1/2}$ | $\delta_h$ MPa$^{1/2}$ |
| Preferred range | 14.5+ | 0-10 | 0-14 |
| More preferred range | 16+ | 0-9 | 0-12 |
| Most preferred range | 17+ | 0-8 | 0-10 |

The three dimensional solubility parameters listed above include: dispersive ($\delta_d$), polar ($\delta_p$) and hydrogen bonding ($\delta_h$) components (C. M. Hansen, Ind. Eng. and Chem., Prod. Res, and Devl., 9, No 3, p 282, 1970). These parameters may be determined empirically or calculated from known molar group contributions as described in Handbook of Solubility Parameters and Other Cohesion Parameters ed. A. F. M. Barton, CRC Press, 1991. The solubility parameters of many known polymers are also listed in this publication.

It is desirable that the permittivity of the binder has little dependence on frequency. This is typical of non-polar materials. Polymers and/or copolymers can be chosen as the binder by the permittivity of their substituent groups. A list of low polarity binders suitable for use in the present invention is given (without limiting to these examples) in Table 2:

TABLE 2

| Binder | typical low frequency permittivity ∈ |
|---|---|
| Polystyrene | 2.5 |
| poly(α-methylstyrene) | 2.6 |
| poly(α-vinylnaphtalene) | 2.6 |
| poly(vinyltoluene) | 2.6 |
| Polyethylene | 2.2-2.3 |
| cis-polybutadiene | 2.0 |
| Polypropylene | 2.2 |
| Polyisoprene | 2.3 |
| poly(4-methyl-1-pentene) | 2.1 |
| poly (4-methylstyrene) | 2.7 |
| poly(chorotrifluoroethylene) | 2.3-2.8 |
| poly(2-methyl-1,3-butadiene) | 2.4 |
| poly(p-xylylene) | 2.6 |
| poly(α-α-α'-α' tetrafluoro-p-xylylene) | 2.4 |
| poly[1,1-(2-methyl propane)bis(4-phenyl)carbortate] | 2.3 |
| poly(cyclohexyl methacrylate) | 2.5 |
| poly(chlorostyrene) | 2.6 |
| poly(2,6-dimethyl-1,4-phenylene ether) | 2.5 |
| Polyisobutylene | 2.2 |
| poly(vinyl cyclohexane) | 2.2 |
| poly(vinylcinnamate) | 2.9 |
| poly(4-vinylbiphenyl) | 2.7 |

Other polymers suitable as binders include: poly(1,3-butadiene) or polyphenylene. Copolymers containing the repeat units of the above polymers are also suitable as binders. Copolymers offer the possibility of improving compatibility with the polyacene, modifying the morphology and/or the glass transition temperature of the final layer composition. It will be appreciated that in the above table certain materials are insoluble in commonly used solvents for preparing the layer. In these cases analogues can be used as copolymers. Some examples of copolymers are given in Table 3 (without limiting to these examples). Both random or block copolymers can be used. It is also possible to add some more polar monomer components as long as the overall composition remains low in polarity.

TABLE 3

| Binder | typical low frequency permittivity (∈) |
|---|---|
| Poly(ethylene/tetrafluoroethylene) | 2.6 |
| poly(ethylene/chlorotrifluoroethylene) | 2.3 |
| fluorinated ethylene/propylene copolymer | 2-2.5 |
| polystyrene-co-α-methylstyrene | 2.5-2.6 |
| ethylene/ethyl acrylate copolymer | 2.8 |
| poly(styrene/10% butadiene) | 2.6 |
| poly(styrene/15% butadiene) | 2.6 |
| poly(styrene/2,4 dimethylstyrene) | 2.5 |
| Topas ™ (all grades) | 2.2-2.3 |

Other copolymers may include: branched or non-branched polystyrene-block-polybutadiene, polystyrene-block(poly-ethylene-ran-butylene)-block-polystyrene, polystyrene-block-polybutadiene-block-polystyrene, polystyrene-(ethylene-propylene)-diblock-copolymers (e.g. KRATON®-

G1701E, Shell), polypropylene-co-ethylene) and poly(styrene-co-methylmethacrylate).

Preferred insulating binders for use in the organic semiconductor layer formulation according to the present invention are poly(α-methylstyrene), polyvinylcinnamate, poly(4-vinyiblphenyl), poly(4-methylstyrene), and Topas™ 8007. However, the most preferred insulating binders are poly(α-methylstyrene), polyvinylcinnamate and poly(4-vinylbiphenyl).

As mentioned above the organic binder may itself be a semiconductor, where it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility, μ, of at least $10^{-5}$ cm$^2$V$^{-1}$s$^{-1}$, more preferably at least $10^{-4}$ cm$^2$V$^{-1}$s$^{-1}$.

A preferred class of semiconducting binder has repeat units of Formula 10:

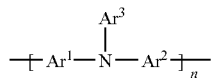

Formula 10 wherein $Ar^1$, $Ar^2$ and $Ar^3$, which may be the same or different, each represent, independently if in different repeat units, an optionally substituted aromatic group (mononuclear or polynuclear) and in the semiconductor binder n is an integer of at least 6, preferably at least 10, more preferably at least 15 and most preferably at least 20. In the context of $Ar^1$, $Ar^2$ and $Ar^3$, a mononuclear aromatic group has only one aromatic ring, for example phenyl or phenylene. A polynuclear aromatic group has two or more aromatic rings which may be fused (for example napthyl or naphthylene), individually covalently linked (for example biphenyl) and/or a combination of both fused and individually linked aromatic rings. Preferably each $Ar^1$, $Ar^2$ and $Ar^3$ is an aromatic group which is substantially conjugated over substantially the whole group.

Preferred classes of semiconducting binders are those containing substantially conjugated repeat units. The semiconducting polymer may be a homopolymer or copolymer (including a block-copolymer) of the general Formula 11:

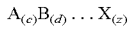

Formula 11 where A, B, . . . , Z each represent a monomer unit and (c), (d), . . . (z) each represent the mole fraction of the respective monomer unit in the polymer, that is each (c), (d), . . . (z) is a value from 0 to 1 and the total of (c)+(d)+ . . . +(z)=1, Examples of monomer units A, B, . . . Z include units of Formula 10 and Formulae 12 to 17 given below:

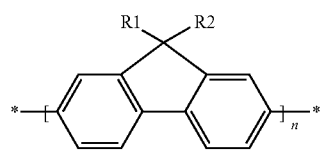

Formula 12 wherein R1 and R2 may be independently: H; optionally substituted alkyl; alkoxy; thioalkyl; acyl; optionally substituted aryl; a fluorine atom; a cyano group; a nitro group; an optionally substituted secondary or tertiary alkylamine or arylamine of formula —N($R_a$)($R_b$), wherein $R_a$ and $R_b$ may each be independently represented by H, optionally substituted alkyl, aryl, optionally substituted aryl, alkoxy or polyalkoxy groups; or other substituent and * is any terminal or end capping group including hydrogen, (the alkyl and aryl groups may be optionally fluorinated);

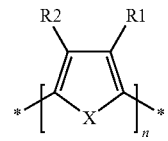

Formula 13 in which X may be Se, Te, C, S or —N($R_c$) more preferably X is O, S or —N($R_c$)—, wherein $R_c$ represents H, optionally substituted alkyl or optionally substituted aryl; and R1 and R2 are as previously described in relation to Formula 12;

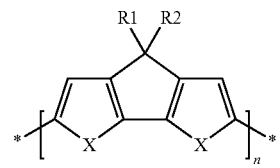

Formula 14 in which R1, R2 and X are as previously described in relation to Formulae 12 and 13 respectively;

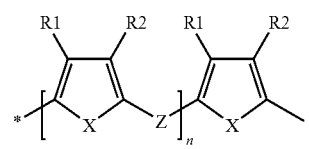

Formula 15 in which R1, R2 and X are as previously described in relation to Formulae 12 and 13 respectively; and Z represents —C($T_1$)=C($T_2$)-, —C≡C—, —N(R')—, —N=N—, (R')=N—, —N=(C(R')—, wherein $T_1$ and $T_2$ independently represent —H, Cl, F, —C≡N or a lower alkyl and R' represents —H, alkyl, substituted alkyl, aryl, or substituted aryl;

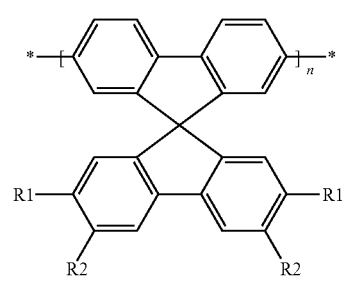

Formula 16 wherein R1 and R2 are as previously described in relation to Formulae 12;

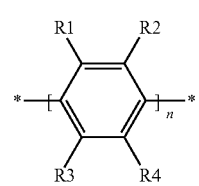

Formula 17 wherein R1 to R4 may be independently selected from the same list of groups as described for R1 and R2 in Formula 12.

In the case of the polymeric Formulae described herein, such as Formulae 10 to 17, the polymers may be terminated by any terminal group, that is any end-capping or leaving group, including hydrogen.

In the case of a block-copolymer, each monomer A, B, ... Z may be a conjugated oligomer or polymer comprising a number, for example 2 to 50, of the units of Formulae 12-17. The semiconducting binder preferably includes; arylamine, fluorene, thiophene, spiro bifluorene and/or optionally substituted aryl (for example, phenylene) groups, more preferably arylamine, still more preferably triarylamine groups. The aforementioned groups may be linked by further conjugating groups for example vinylene. In addition, it is preferred that the semiconducting binder comprises a polymer (either a homo-polymer or copolymer, including block-copolymer) containing one or more of the aforementioned arylamine, fluorene, thiophene and/or optionally substituted aryl groups. A preferred semiconducting binder comprises a home-polymer or copolymer (including block copolymer) containing arylamine (preferably triarylamine) and/or fluorene units. Another preferred semiconducting binder comprises a homo-polymer or copolymer (including block-copolymer) containing fluorene and/or thiophene units.

The semiconducting binder may also contain: carbazole, stilbene repeat units. For example polyvinylcarbazole or polystilbene polymers, copolymers may be used. The semiconducting binder may optionally contain polyacene segments (for example repeat units as described for Formula A above) to improve compatibility with the soluble polyacene molecules.

The most preferred semiconducting binders for use in the organic semiconductor layer formulation according to the present invention are poly(9-vinylcarbazole) and PTAA1.

For application of the semiconducting layer in p-channel FETs, it is desirable that the semiconducting binder should have a higher ionisation potential than the polyacene semiconductor, otherwise the binder may form hole traps. In n-channel materials the semiconducting binder should have lower electron affinity than the n-type semiconductor to avoid electron trapping.

The formulation according to the present invention may be prepared by a process which comprises:
(i) first mixing both a polyacene compound and an organic binder, preferably the mixing comprises mixing the two components together in a solvent or solvent mixture. The solvent may be a single solvent or the polyacene compound and the organic binder may each be dissolved in a separate solvent followed by mixing the two resultant solutions to mix the compounds; and
(ii) applying the solvent(s) containing the polyacene compound and the organic binder to a substrate; and
(iii) optionally evaporating the solvent(s) to form the layer of the invention.

The binder may be formed in situ by mixing or dissolving a polyacene in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer.

If a preformed binder is used it may be dissolved together with the polyacene in a suitable solvent, and the solution deposited for example by dipping, spraying, painting or printing it on a substrate to form a liquid layer and then removing the solvent to leave a solid layer. It will be appreciated that solvents are chosen which are able to dissolve both the binder and polyacene, and which upon evaporation from the solution blend give a coherent defect free layer. Suitable solvents for the binder or polyacene can be determined by preparing a contour diagram for the material as described in ASTM Method D 3132 at the concentration at which the mixture will be employed. The material is added to a wide variety of solvents as described in the ASTM method.

It will also be appreciated that in accordance with the present invention the formulation may comprise one or more polyacene compounds and/or one of more binders and that the process for preparing the formulation may be applied to such formulations.

Examples of organic solvents which may be considered are: $CH_2Cl_2$, $CHCl_3$, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin and/or mixtures thereof. After the appropriate mixing and aging, solutions are evaluated as one of the following categories: complete solution, borderline solution or insoluble. The contour line is drawn to outline the solubility parameter-hydrogen bonding limits dividing solubility and insolubility, 'Complete' solvents falling within the solubility area can be chosen from literature values such as published in "Crowley, J. D., Teague, G. S, Jr and Lowe, J. W. Jr., Journal of Paint Technology, 38, No 495, 296 (1966)". Solvent blends may also be used and can be identified as described in "Solvents, W. H. Ellis, Federation of Societies for Coatings Technology, p 9-10, 1986". Such a procedure may lead to a blend of 'non' solvents that will dissolve both the binder and polyacene, although it is desirable to have at least one true solvent in a blend.

Preferred solvents for use in the organic semiconducting layer formulation according to the present invention for use with both insulating and semiconducting binders and mixtures thereof are: xylene(s), toluene, tetralin and o-dichlorobenzene.

The proportions of binder to polyacene in the formulation or layer according to the present invention are typically 20:1 to 1:20 by weight, preferably 10:1 to 1:10 more preferably 5:1 to 1:5, still more preferably 3:1 to 1:3 further preferably 2:1 to 1:2 and especially 1:1. Surprisingly and beneficially, dilution of the polyacene in the binder has been found to have little or no detrimental effect on the charge mobility, in contrast to what would have been expected from the prior art.

In accordance with the present invention it has further been found that the level of the solids content in the organic semiconducting layer formulation is also a factor in achieving improved mobility values for electronic devices such as OFETs. The solids content of the formulation is commonly expressed as follows:

$$\text{Solids content (\%)} = \frac{a+b}{a+b+c} \times 100$$

wherein:
a=mass of polyacene, b=mass of binder and c=mass of solvent.

The solids content of the formulation is preferably 0.1 to 10% by weight, more preferably 0.5 to 5% by weight.

Surprisingly and beneficially, dilution of the polyacene in the binder has been found to have little or no effect on the charge mobility, in contrast to what would have been expected from the prior art.

It is desirable to generate small structures in modern microelectronics to reduce cost (more devices/unit area), and power consumption. Patterning of the layer of the invention may be carried out by photolithography or electron beam lithography.

Liquid coating of organic electronic devices such as field effect transistors is more desirable than vacuum deposition techniques. The polyacene and binder mixtures of the present invention enable the use of a number of liquid coating techniques. The organic semiconductor layer may be incorporated into the final device structure by, for example and without limitation, dip coating, spin coating, ink jet printing, letter-press printing, screen printing, doctor blade coating; roller printing, reverse-roller printing; offset lithography printing, flexographic printing, web printing, spray orating, brush coating or pad printing. The present invention is particularly suitable for use in spin coating the organic semiconductor layer into the final device structure.

Selected polyacene and binder compositions of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, polyacene and binder compositions must first be dissolved in a suitable solvent. Solvents must fulfill the requirements stated above and must not have any detrimental effect on the chosen print head. Additionally, solvents should have boiling points >100° C., preferably >140° C. and more preferably >150° C. in order to prevent operability problems caused by the solution drying out inside the print head. Suitable solvents include substituted and non-substituted xylene derivatives, formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a binder/polyacene formulation by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the binder and polyacene which reduces or prevents clogging of the jets and separation of the components during spraying. The solvent(s) may include those selected from the following list of examples: dodecylbenzene; 1-Methyl-4-tert-butylbenzene; Terpineol; Limonene; Isodurene; Terpinolene; Cymene; Diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and polyacene) preferably has a viscosity at 20° C. of 1-100 mPa·s, more preferably 1-50 mPa·s and most preferably 1-30 mPa·s The use of the binder in the present invention also allows the viscosity of the coating solution to be tuned to meet the requirements of the particular print head.

The semiconducting layer of the present invention is typically at most 1 micron (=1 μm) thick, although it may be thicker if required. The exact thickness of the layer will depend, for example, upon the requirements of the electronic device in which the layer is used. For use in an OFET or OLED, the layer thickness may typically be 500 nm or less.

In the semiconducting layer of the present invention there may be used two or more different polyacene compounds of Formula 1-9. Additionally or alternatively, in the semiconducting layer there may be used two or more organic binders of the present invention.

As mentioned above, the invention further provides a process for preparing the organic semiconducting layer which comprises (i) depositing on a substrate a liquid layer of a mixture which comprises a polyacene compound, an organic binder resin or precursor thereof and optionally a solvent, and (ii) forming from the liquid layer a solid layer which is the organic semiconducting layer.

In the process, the solid layer may be formed by evaporation of the solvent and/or by reacting the binder resin precursor (if present) to form the binder resin in situ. The substrate may include any underlying device layer, electrode or separate substrate such as silicon wafer or polymer substrate for example.

In one particular embodiment of the present invention, the binder may be alignable, for example capable of forming a liquid crystalline phase. In that case the binder may assist alignment of the polyacene, for example such that the polyacene backbone is preferentially aligned along the direction of charge transport. Suitable processes for aligning the binder include those processes used to align polymeric organic semiconductors such as described in WO 03/007397 (Plastic Logic).

The present invention also provides the use of the semiconducting formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising the formulation according to the invention. The layer or film may be less than about thirty microns. For various electronic device applications, the thickness may be less than about one micron thick. The layer may be deposited, for example on a part of an electronic device, by any of the aforementioned solution coating or printing techniques.

The formulation may be used, for example as a layer or film, in a field effect transistor (FET) for example as the semiconducting channel, organic light emitting diode (OLED) for example as a hole or electron injection or transport layer or electroluminescent layer, photodetector, chemical detector, photovoltaic cell (PVs), capacitor sensor, logic circuit, display, memory device and the like. The formulation may also be used in electrophotographic (EP) apparatus. The formulation is preferably solution coated to form a layer or film in the aforementioned devices or apparatus to provide advantages in cost and versatility of manufacture. The improved charge carrier mobility of the formulation of the present invention enables such devices or apparatus to operate faster and/or more efficiently. The formulation and layer of the present invention are especially suitable for use in an organic field effect transistor OFET as the semiconducting channel. Accordingly, the invention also provides an organic field effect transistor (OFET) comprising a source electrode, a drain electrode and an organic semiconducting channel connecting the source and drain electrodes, wherein the organic semiconducting channel comprises an organic semiconducting layer according to the present invention. Other features of the OFET are well known to those skilled in the art.

Some definitions and explanations of terms used herein are now given.

When in the formulae herein there is a list of labels (for example $R_1$, $R_2$ etc.) or indices (for example 'n') which are said to represent a list of groups or numerical values, and these are said to be "independent in each case" this indicates each label and/or index can represent any of those groups listed independently from each other, independently within each repeat unit, independently within each Formula and/or independently on each group which is substituted as appropriate. Thus, in each of these instances, many different groups might be represented by a single label (for example $R_5$).

The terms 'substituent', 'substituted', 'optional substituent' and/or 'optionally substituted' as used herein (unless followed by a list of other substituents) signifies at least one of the following groups (or substitution by these groups): silyl, sulpho, sulphonyl, formyl, amino, imino, nitrilo, mercapto, cyano, nitro, halo, $C_{1-4}$alkyl, $C_{6-12}$ aryl, $C_{1-4}$alkoxy, hydroxy and/or combinations thereof. These optional groups may comprise all chemically possible combinations in the same group and/or a plurality (preferably two) of the aforementioned groups (for example amino and sulphonyl if directly attached to each other represent a sulphamoyl radical). Preferred optional substituents comprise: $C_{1-4}$alkyl; methoxy and/or ethoxy (any of these optionally substituted by at least one halo); amino (optionally substituted by at least one methyl and/or ethyl); and/or halo.

The term 'carbyl group' as used herein denotes any monovalent or multivalent organic radical moiety which comprises at least one carbon atom either without any non-carbon atoms (for example —C≡C—), or optionally combined with at least one other non-carbon atom (for example alkoxy, carbonyl etc.).

The term 'hydrocarbon group', 'hydrocarbyl' or the like may be used herein interchangeably. A hydrocarbon group may be optionally substituted. A hydrocarbon group may also contain at least one of the following heteroatom containing moieties: oxy, thio, sulphinyl, sulphonyl, amino, imino, nitrilo and/or combinations thereof.

The terms 'alkyl', 'aryl', etc. as used herein may be readily replaced, where appropriate, by terms denoting a different degree of valence for example multivalent species (for example alkylene, arylene, etc.).

The term 'halo' as used herein signifies fluoro, chloro, bromo and iodo.

Unless the context clearly indicates otherwise, a group herein which comprises a chain of three or more carbon atoms signifies a group in which the chain wholly or in part may be linear, branched and/or form a ring (including spiro and/or fused rings).

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

EXAMPLES

Synthesis of Organic Semiconductor Materials

1. Synthesis of 6,13-bis(triisopropylsilylethynyl) pentacene—Compound 1

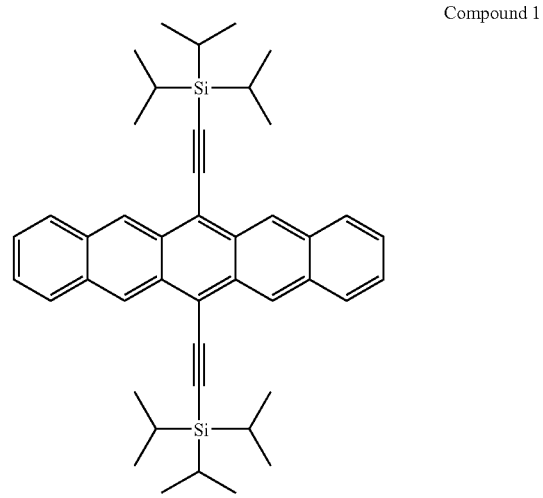

Compound 1

To a flame-dried flask fitted with mechanical stirrer, nitrogen inlet and outlet, condenser and suba-seal was added isopropylmagnesium chloride (2M in THF (10 molar equivalents based on 6,13-pentacenequinone)). This solution was cooled using a cold-water bath to act as a cold trap to absorb any exotherm during the triisopropylsilyl acetylene addition. Triisopropylsilyl acetylene (10.1 molar equivalents based on 6,13-pentacenequinone) was added to the reaction flask dropwise over 30 minutes followed by the addition of THF (10 ml for every 10 mmol of TIPS acetylene). The cold-water bath was removed and the solution heated at 60° C. for 20 minutes. The flask was then allowed to cool to room temperature. 6,13-Pentacenequinone (1 molar equivalent) was added to the Grignard reagent and the resulting cloudy suspension was heated at 60° C. until the reaction was deemed complete according to HPLC, (up to 3 hours). The flask was allowed to cool to room temperature. A solution of 10% aqueous HCl saturated with tin (II) chloride was added cautiously to the brown/red reaction solution until the solution no longer exothermed on addition. (It was noted that as the tin (II) chloride solution was added, the reaction solution turned from brown/red to a deep blue colour). The resulting solution was heated at 60° C. for 30 minutes before cooling to room temperature. This crude mixture was isolated from a water/DCM mixture drying the organic phase over magnesium sulphate (MgSO$_4$) before filtering and concentrating under vacuum to give a blue/black solid. Purification by column chromatography (silica gel, 5% DCM in hexane) followed by recrystallisation from acetone yielded the title compound as dark blue plates.

2. Alternative Route to the Synthesis of 6,13-bis(triisopropylsilyl)ethynyl pentacene Compound 1

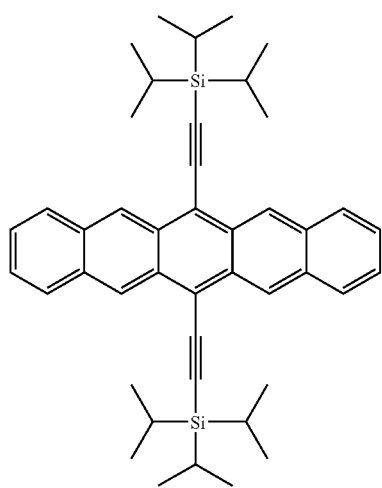

Compound 1

To a flame-dried flask was added (triisopropylsilyl)acetylene (6 molar equivalents (2.18 ml, 9.72 mmol)) and tetrahydrofuran (THF) (15 ml) and the solution cooled to −78° C. 2.5M n-butyllithium in hexane (5.5 molar equivalents (3.56 ml, 6.91 mmol)) was then added drop-wise over 20 minutes. The resulting solution was stirred at −78° C. for a further 45 minutes. 6,13-Pentacenequinone (1 molar equivalent (0.50 g, 1.62 mmol)) was added and the reaction mixture was allowed to warm up to room temperature with stirring overnight. A solution of 10% aqueous HCl saturated with SnCl$_2$ (5 ml) was then added at room temperature and the reaction mixture stirred at 50° C. for 30 minutes. On cooling, 2M aqueous Na$_2$CO (5 ml) was added and the resulting crude solution was filtered through celite and then concentrated under vacuum. Purification by chromatography (flash silica, hexane:DCM, 95:5) followed by an acetone wash gave the title compound as a dark blue powder (0.73 g, 70%) and was greater than 99% pure by HPLC. $^1$H NMR (CDCl$_3$) δ 9.30 (4H, s, H—Ar), 7.95 (4H, m, H—Ar), 7.41 (4H, m, H—Ar) and 1.42 ppm (42H, m, H-aliphatic); $^{13}$C NMR (CDCl$_3$) δ 132.48, 130.83, 128.89, 126.52, 126.23, 118.56, 107.38, 104.90, 19.22 and 11.89 ppm.

3. Synthesis of 2,3,9,10-tetramethyl-6,13-bis(triisopropylsilylethynyl)pentacene—Compound 4

3a. Synthesis of 4,5-dimethylphthalaldehyde—Compound 2

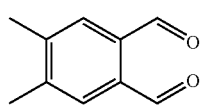

Compound 2

To a solution of oxalyl chloride 2M in dichloromethane (DCM) (26.5 ml, 53.0 mmol, 2.2 molar equivalents) cooled to −78° C. was added dropwise a solution of dimethylsulfoxide (DMSO) (7.5 ml, 105.8 mmol, 4.4 molar equivalents) in DCM (10 ml). The solution was stirred at −78° C. for 5 minutes and 4,5-dimethylbenzene-1,2-dimethanol (4.0 g, 24.1 mmol, 1.0 molar equivalent) dissolved in a mixture of DCM-DMSO (2 ml-4 ml) was added dropwise. The solution was stirred for 1 hour at −78° C. and triethylamine (20 ml) was slowly added at −78° C. The reaction mixture was stirred for 10 minutes at −78° C. and slowly warmed up to room temperature. Ice-cold water (100 ml) was added to the reaction mixture and the aqueous layer extracted with DCM (3 times 100 ml). The organic fractions were combined, dried over magnesium sulfate, filtered and concentrated in vacuum to give a brown oil. Purification by column chromatography on silica gel (eluent: hexane-ethyl acetate 8:2) gave the title compound as white needles (3.2 g, 82%). $^1$H NMR (300.13 MHz, CDCl$_3$) δ(ppm) 2.42 (s, 6H) 7.73 (s, 2H) 10.50 (s, 2H).

3b. Synthesis of 2,3,9,10-tetramethyl-6,13-pentacenequinone—Compound 3

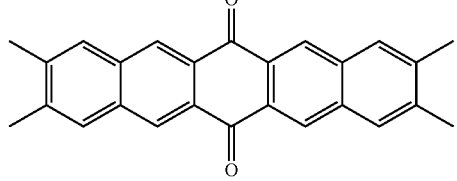

Compound 3

To a solution of 4,5-dimethylphthalaldehyde (Compound 2) (1.59 g, 9.8 mmol, 2 molar equivalents) and 1,4-cyclohexanedione (0.54 g, 4.8 mmol, 1 molar equivalent) in ethanol (150 ml) was added a solution of 5% aqueous NaOH (3 ml) at room temperature. The reaction mixture was stirred for 30 minutes at room temperature and then warmed to 60° C. After 1 hour at 60° C., the reaction mixture was cooled to room temperature. The resulting precipitate was filtered, washed with water (25 ml), ethanol (50 ml) and diethyl ether (50 ml) to give the title compound as a yellow powder (1.63 g, 93%). IR (selected bands) 1672 (quinone), 1579, 1452, 1396, 1221, 738 cm$^{-1}$.

3c. Synthesis of 2,3,9,10-tetramethyl-6,13-bis(triisopropylsilylethynyl)pentacene—Compound 4

Compound 4

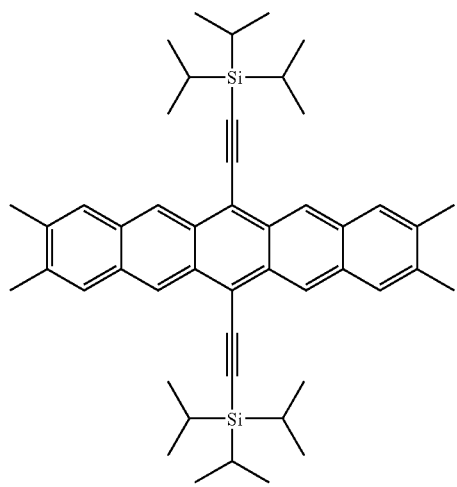

To a solution of triisopropylsilylacetylene (3.7 ml, 16.4 mmol, 6 molar equivalents) in tetrahydrofuran (THF) (100 ml) cooled to −78° C. was added dropwise a 2.5M solution of n-butyllithium in hexane (6 ml, 15 mmol, 5.5 molar equivalents). The solution was stirred at −78° C. for 45 minutes and 2,3,9,10-tetramethyl-6,13-pentacenequinone (Compound 3) (1 g, 2.7 mmol, 1 molar equivalent) was added. The reaction mixture was warmed up and stirred overnight at room temperature. A solution of 10% aqueous HCl saturated with $SnCl_2$ (10 ml) was added at room temperature and the reaction mixture was stirred at 50° C. for 45 minutes. On cooling, a solution of 2M aqueous solution of $Na_2CO_3$ (10 ml) was added and the resulting solution stirred with celite for 5 minutes. The solution was filtered through celite and concentrated under vacuum to give a dark blue solid. Purification by column chromatography on silica gel (eluent, hexane:DCM 6:4) followed by an acetone wash gave the title compound as a dark blue powder (0.8 g, 42%). Greater than 99% pure by HPLC, $^1$H NMR (300.13 MHz, $CDCl_3$) δ(ppm) 1.36-1.39 (m, 42H) 7.67 (s, 4H) 9.12 (s, 4H); $^{13}$C NMR (125.77 MHz, $CDCl_3$) δ(ppm) 11.72, 19.04, 20.56, 105.11, 106.23, 117.68, 124.49, 127.09, 130.42, 131.84, 136.37

4. Synthesis of 5,11-bis(triisopropylsilylethynyl)anthra[2,3-b:6,7-b']dithiophene—Compound 7 and 5,11-bis(triisopropylsilylethynyl)anthra[2,3-b:7,6-b']dithiophene—Compound 8

4a. Synthesis of Anthra[2,3-b:6,7-b']dithiophene-5,11-dione—Compound 5 and Anthra[2,3-b:7,6-b']dithiophene-5,11-dione—Compound 6

Compound 5

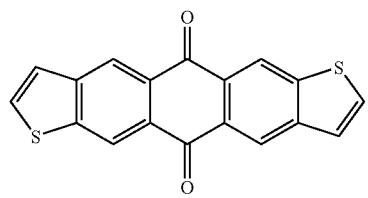

Compound 6

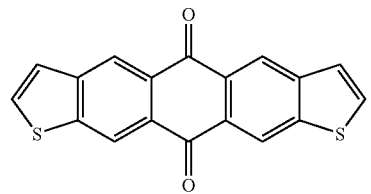

To a solution of thiophene-2,3-dicarbaldehyde (1.00 g, 7.1 mmol, 2 molar equivalents) and 1,4-cyclohexanedione (0.40 g, 3.6 mmol, 1 molar equivalent) in ethanol (100 ml) was added a solution of 5% aqueous NaOH (3 ml) at room temperature. The reaction mixture was stirred for 30 minutes at room temperature and then warmed to 60° C. After 1 hour at 60° C., the reaction mixture was cooled to room temperature. The resulting precipitate was filtered, washed with water (20 ml), ethanol (40 ml) and diethyl ether (40 ml) to give the title compound as a yellow powder (1.02 g, 89%). IR (selected bands) 1667 (quinone), 1573, 1318, 1283 $cm^{-1}$.

4b. Synthesis of 5,11-bis(triisopropylsilylethynyl)anthra[2,3-b:6,7-b']dithiophene—Compound 7 and 5,11-bis(triisopropylsilylethynyl)anthra[2,3-b:7,6-b']dithiophene—Compound 8

Compound 7

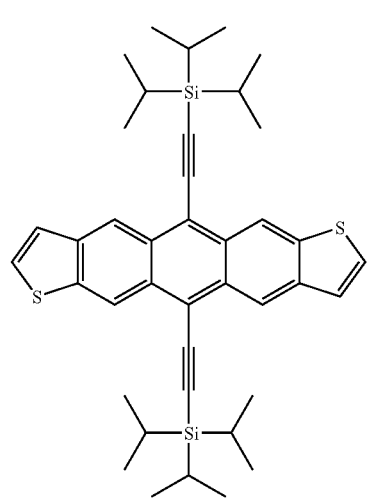

Compound 8

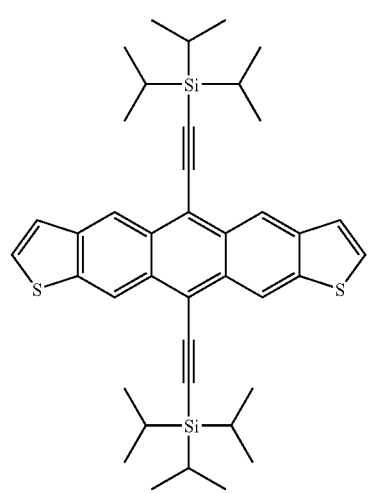

To a solution of triisopropylsilylacetylene (2.1 ml, 9.4 mmol, 6 molar equivalents) in tetrahydrofuran (THF) (50 ml) cooled to −78° C. was added dropwise a 2.5M solution of n-butyllithium in hexane (3.4 ml, 8.5 mmol, 5.5 molar equivalents). The solution was stirred at −78° C. for 45 minutes and anthradithiophene-5,11-diones (Compounds 5 and 6) (0.5 g, 1.6 mmol, 1 molar equivalent) were added. The reaction mixture was warmed and stirred overnight at room temperature. A solution of 10% aqueous HCl saturated with $SnCl_2$ (5 ml) was added at room temperature and the reaction mixture was stirred at 50° C. for 45 minutes. On cooling, a solution of 2M aqueous solution of $Na_2CO_3$ (5 ml) was added and the resulting solution was stirred with celite for 5 minutes. The solution was filtered through celite and concentrated under vacuum to give a dark red solid. Purification by column chromatography on silica gel (eluent, hexane:DCM 8:2) followed by an acetone wash gave the title compound as a dark red powder (0.45 g, 44%). Greater than 99% pure by HPLC (Syn and anti isomers co-elute), $^1$H NMR (500.13 MHz, $CDCl_3$) δ (ppm) 1.37-1.39 (s, 42H) 7.42 (d, J=5.50 Hz, 2H) 7.54 (dd, $J_1$=5.50, $J_2$=2.00 Hz, 2H) 9.15 (s, 2H) 9.19 (s, 2H); $^{13}$C NMR (125.77 MHz, $CDCl_3$) δ(ppm) 11.26, 11.65, 18.74, 18.96, 104.13, 104.20, 105.61, 105.89, 106.16, 117.62, 118.92, 120.02, 120.06, 121.31, 121.37, 123.75, 129.76, 129.78, 129.85, 129.88, 129.96, 130.06, 139.46, 139.61, 139.96, 140.06

5. Synthesis of 6,13-bis(trimethylsilyl)ethynyl pentacene—Compound 9

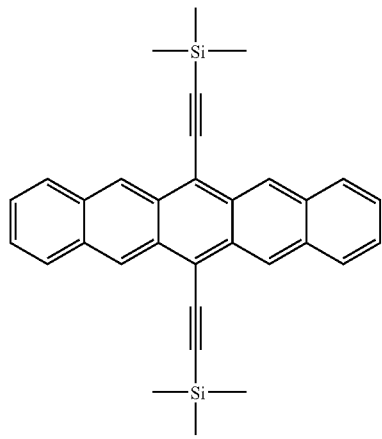

Compound 9

To a flame-dried flask was added (trimethylsilyl)acetylene (6 molar equivalents (13.7 ml, 97.3 mmol)) and tetrahydrofuran (THF) (110 ml) and the solution cooled to −78° C. 2.5M n-butyllithium in hexane (5.5 molar equivalents (36.0 ml, 89.2 mmol)) was then added drop-wise over 20 minutes. The resulting solution was stirred at −78° C. for a further 45 minutes. 6,13-Pentacenequinone (1 molar equivalent (5.0 g, 16.2 mmol)) was then added and the reaction mixture allowed to warm up to room temperature with stirring overnight. A solution of 10% aqueous HCl saturated with $SnCl_2$ (50 ml) was added at room temperature and the reaction mixture was stirred at 50° C. for 30 minutes. On cooling, 2M aqueous $Na_2CO_3$ (50 ml) was added and the resulting crude solution was filtered through celite and then concentrated under vacuum. Purification by chromatography (flash silica, hexane:DCM, 80:20) followed by an acetone wash gave the title compound as a dark blue powder (3.8 g, 50%) and was greater than 99% pure by HPLC. $^1$H NMR ($CDCl_3$) δ 9.21 (4H, s, H—Ar), 8.05 (4H, m, H—Ar), 7.42 (4H, m, H—Ar) and 0.53 ppm (18H, s, H-aliphatic).

6. Synthesis of 6,13-bis(triethylsilyl)ethynyl pentacene—Compound 10

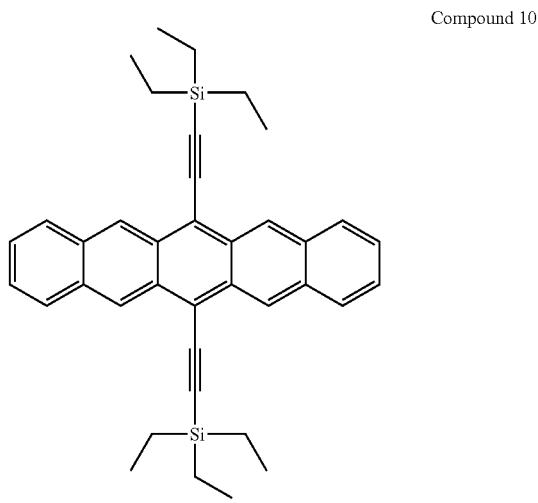

Compound 10

To a flame-dried flask was added isopropylmagnesium chloride (2M solution in THF; 10 molar equivalents (13.7 ml, 27.4 mmol)) and tetrahydrofuran (THF) (60 ml). Triethylsilylacetylene (10 molar equivalents, 5.6 ml, 31.3 mmol) was then added dropwise. The mixture was then heated to reflux for 20 minutes. The resulting solution was allowed to cool to room temperature and 6,13 pentacenequinone (1 molar equivalent (1.0 g, 3.24 mmol)) was added. The reaction mixture was then heated to reflux for 1 hour before allowing to cool to room temperature. A solution of 10% aqueous HCl saturated with $SnCl_2$ (50 ml) was added at room temperature and the reaction mixture was stirred at 50° C. for 30 minutes. On cooling, saturated potassium hydrogen carbonate solution ($KHCO_3$) (25 ml) was added and the resulting crude solution was filtered through celite and then concentrated under vacuum. Purification by flash column chromatography (eluent 20% $CH_2Cl_2$:hexane) followed by washing with acetone gave the title compound as a dark blue powder (1.1 g, 61%) that was greater than 99% pure by HPLC, $^1$H NMR (300 MHz, $CDCl_3$) δ 9.25 (4H, s, H—Ar), 8.00 (4H, m, H—Ar), 7.40 (4H, m, H—Ar) 1.30 (18H, t, J=6.0 Hz, $SiCH_2\underline{CH_3}$) 0.98 ppm (12H, q, J=6.0 Hz, $Si\underline{CH_2}CH_3$).

7. 6,13-bis(4'-pentylphenyl)ethynyl pentacene—Compound 11

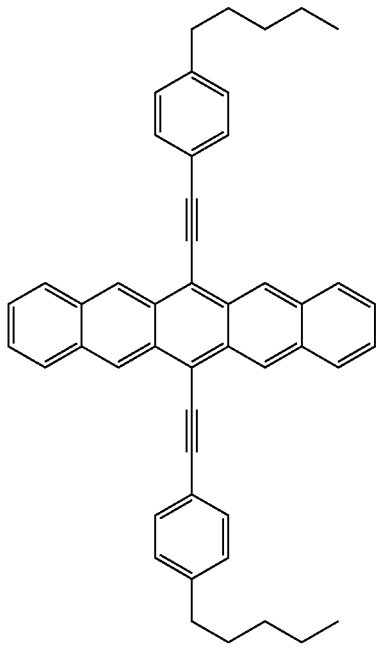

Compound 11

To a flame-dried flask was added isopropylmagnesium chloride (2M solution in THF; 10 molar equivalents (32.4 ml, 64.8 mmol)) and tetrahydrofuran (THF) (60 ml). 1-ethynyl-4-pentylbenzene (10 molar equivalents, 12.4 mL, 63.7 mmol) was then added dropwise. The mixture was then heated to reflux for 20 minutes. The resulting solution was allowed to cool to room temperature and pentacenequinone (1 molar equivalent (2.0 g, 6.5 mmol)) was added. The reaction mixture was then heated to reflux for 30 minutes. The mixture was allowed to cool to room temperature. A solution of 10% aqueous HCl saturated with $SnCl_2$ (20 ml) was added at room temperature and the reaction mixture was stirred at 50° C. for 30 minutes. On cooling, saturated $Na_2CO_3$ solution (50 ml) was added slowly. The material was transferred to a 1 L separating funnel, then water (100 ml) and $CH_2Cl_2$ (50 ml) were added. The organic and aqueous phases were separated and the aqueous phase was extracted with $CH_2Cl_2$ (3×50 ml). The combined organic phases were then washed with water (100 ml), filtered through a Whatman No. 1 filter paper and concentrated to give a blue solid. This material was stirred with acetone (50 ml) and filtered to give a blue solid, (3.0 g, 75%). 1 g of this material was purified by flash column chromatography (flash silica, eluent 40% $CH_2Cl_2$:hexane) to give the product as a blue solid (0.8 g, 80% recovery) that was greater than 99% pure by HPLC. $^1H$ NMR (300 MHz, $CDCl_3$) δ 9.20 (4H, s, H—Ar), 7.90 (4H, m, H—Ar), 7.35 (4H, m, H—Ar) 2.73 (4H, t, J=6.0 Hz, —C C$\underline{H}_2$—) 1.72 (4H, m, C C$\underline{H}_2$C$\underline{H}_2$—), 1.40 (8H, m, C C$\underline{H}_2$C$\underline{H}_2$C$\underline{H}_2$—), 0.95 ppm (12H, t, J=3.0 Hz, $CH_2C\underline{H}_3$).

8. Synthesis of Naphtho[2,1,8-qra]naphthacene-7,12-(triisopropylsilyl)ethynyl—Compound 12

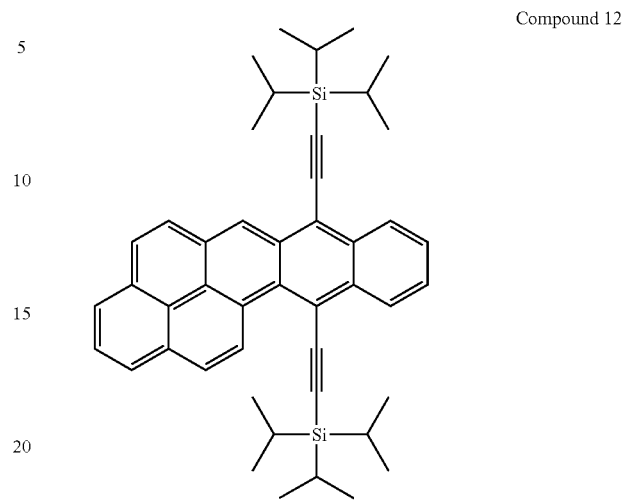

Compound 12

To a flame-dried flask was added (triisopropylsilyl)acetylene (6 molar equivalents (2.03 ml, 9.03 mmol)) and tetrahydrofuran (THF) (50 ml) this solution was cooled to −78° C., 2.5M n-butyllithium in hexanes (5.5 molar equivalents (5.16 ml, 8.25 mmol)) was added drop-wise over 20 minutes. The resulting solution was stirred at −78° C. for a further 45 minutes. Naphtho[2,1,8-qra]naphthacene-7,12-dione (1 molar equivalent (0.50 g, 1.50 mmol)) was then added and the reaction mixture allowed to warm up to room temperature with stirring overnight. A solution of 10% aqueous HCl saturated with $SnCl_2$ (10 ml) was added at room temperature and the reaction mixture was stirred at 50° C. for 30 minutes. On cooling, 2M aqueous $Na_2CO_3$ (5 ml) was added and the resulting crude solution was filtered through celite and then concentrated under vacuum. Purification by chromatography (flash silica, hexane:DCM, 95:5) followed by an acetone wash gave the title compound as a red powder (0.23 g, 23%) and was greater than 99% pure by HPLC. $^1H$ NMR ($CDCl_3$) δ 11.09 (1H, d, H—Ar), 9.30 (1H, s, H—Ar), 9.08 (1H, m, H—Ar), 8.80 (1H, m, H—Ar), 8.20 (2H, m, H—Ar), 7.95 (2H, m, H—Ar), 7.82 (2H, m, H—Ar), 7.71 (2H, m, H—Ar) and 1.47-1.25 ppm (42H, m, H-aliphatic).

9. Synthesis of 5,14-(Triisopropylsilyl)acetylene pentacene—Compound 14

9a. Synthesis of 5,14-Pentacenequinone—Compound 13

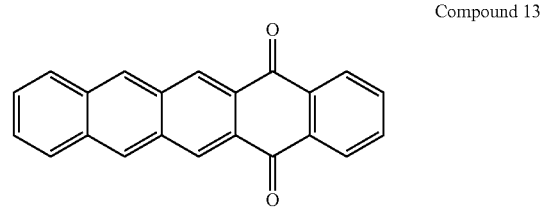

Compound 13

To a flame-dried flask was added 2,3-naphthalenedicarboxaldehyde (1 molar equivalent (0.29 g, 1.57 mmol)) and 1,4-dihydroxynaphthalene (1 molar equivalent (0.25 g, 1.57 mmol)) these reagents were flushed with nitrogen for 15 minutes before anhydrous pyridine (5 ml) was added. The resulting solution was stirred at 120° C. with stirring for 24 hours. On cooling, the solid product was filtered off and washed successively with methanol (10 ml), 10% copper sulphate solution (10 ml), water (10 ml) and acetone (10 ml) and dried in vacuum oven. The product was an orange/brown solid (0.14 g, 29%) and was greater than 90% pure by HPLC. $^1$H NMR (D8-THF) δ 9.09 (2H, s, H—Ar), 8.87 (2H, s, H—Ar), 8.38 (2H, m, H—Ar), 8.15 (2H, m, H—Ar), 7.87 (2H, m, H—Ar) and 7.61 ppm (2H, m, H—Ar).

9b. Synthesis of 5,14-(Triisopropylsilyl)acetylene pentacene—Compound 14

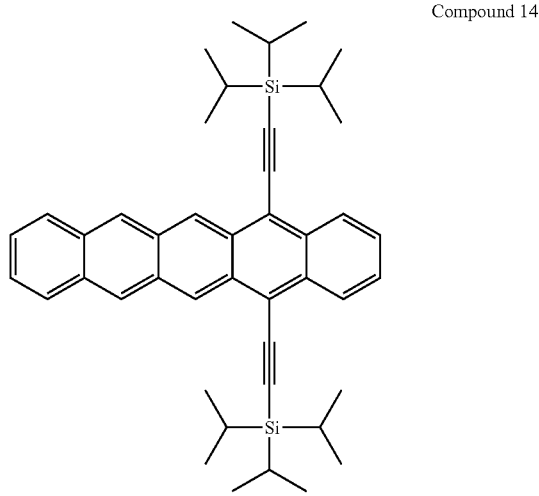

Compound 14

To a flame-dried flask was added (triisopropylsilyl)acetylene (6 molar equivalents (1.31 ml, 5.84 mmol)) and tetrahydrofuran (THF) (10 ml) and the solution cooled to −78° C. 2.5M n-butyllithium in hexane (5.5 molar equivalents (3.34 ml, 5.35 mmol)) was added drop-wise over 20 minutes. The resulting solution was stirred at −78° C. for a further 45 minutes. 5,14-Pentacenequinone (Compound (13)) (1 molar equivalent (0.30 g, 0.97 mmol)) was then added and the reaction mixture allowed to warm up to room temperature with stirring overnight. A solution of 10% aqueous HCl saturated with SnCl$_2$ (5 ml) was then added at room temperature and the reaction mixture was stirred at 50° C. for 30 minutes. On cooling, 2M aqueous Na$_2$CO$_3$ (5 ml) was added and the resulting crude solution was filtered through celite and then concentrated under vacuum. Purification by chromatography (flash silica, hexane:DCM, 90:10) followed by an acetone wash gave the title compound as a dark blue powder (0.22 g, 35%) and found to be greater than 99% pure by HPLC. $^1$H NMR (CDCl$_3$) δ 9.58 (2H, s, H—Ar), 8.68 (2H, s, H—Ar), 8.55 (2H, m, H—Ar), 8.00 (2H, m, H—Ar), 7.50 (2H, m, H—Ar), 7.39 (2H, m, H—Ar) and 1.45-1.25 ppm (42H, m, H-aliphatic).

10. Synthesis of 1,8-difluoro-6,13-bis(triisopropylsilylethynyl)pentacene—Compound 19 and 1,11-difluoro-6,13-bis(triisopropylsilylethynyl)pentacene—Compound 20

10a. Synthesis of 3-Fluorobenzene-1,2-dimethanol—Compound 15

Compound 15

To a solution of LiAlH$_4$ (1M in tetrahydrofuran) (54 ml, 54.0 mmol, 2.0 molar equivalents), cooled to −78° C., was added dropwise a solution of 3-fluorophtalic acid (5.0 g, 27.2 mmol, 1 molar equivalent) in THF (25 ml). The reaction mixture was allowed to warm up to room temperature and then stirred at 70° C. for 2 hours. To this resulting solution, cooled at 0° C. was added a 2M sodium hydroxide solution (25 ml) followed by cold water (25 ml) and THF (50 ml). The reaction mixture was then further extracted with THF (3×50 ml). The organic fractions were combined, washed with brine, dried over magnesium sulfate, filtered and concentrated in vacuum to give a light yellow solid. Purification by recrystallisation from acetone/hexane gave the title compound as white needles (3.3 g, 79%). $^1$H NMR (300.13 MHz, DMSO) δ(ppm) 4.53 (dd, J$_1$=5.50, J$_2$=2.00 Hz, 2H) 4.67 (d, J=5.50 Hz, 2H) 4.98 (t, J=5.50 Hz, 1H) 5.22 (t, J=5.50 Hz, 1H) 7.00-7.10 (m, 1H) 7.25-7.35 (m, 2H). $^{19}$F NMR (282.38 MHz, DMSO) δ(ppm) −119.92 (s). $^{13}$C NMR (75.48 MHz, CDCl$_3$) δ(ppm) 52.63, 60.07, 113.26, 122.81, 128.69, 144.02, 158.64, 161.87.

10b. Synthesis of 3-Fluorophthalaldehyde—Compound 16

Compound 16

To a solution of oxalyl chloride 2M in dichloromethane (DCM) (11 ml, 22 mmol, 2.2 molar equivalents) cooled to −78° C., was added dropwise a solution of dimethylsulfoxyde (DMSO) (3.10 ml, 44 mmol, 4.4 molar equivalents) in DCM (10 ml). The solution was then stirred at −78° C. for 5 minutes and 3-fluorobenzene-1,2-dimethanol (Compound 17) (1.55 g, 10 mmol, 1.0 molar equivalent) dissolved in a mixture of DCM-DMSO (1-2 ml) added dropwise. The solution was then stirred for 1 hour at −78° C. and triethylamine (25 ml) was slowly added at −78° C. The reaction mixture was then stirred for 10 minutes at −78° C. and slowly warmed up to room temperature. Ice-cold water (50 ml) was added to the reaction mixture and the aqueous layer extracted with DCM (3 times 50 mls). The organic fractions were combined, dried over magnesium sulfate, filtered and concentrated in vacuum to give a brown oil. Purification by distillation gave the title compound as a light yellow solid (1.10 g, 73%). $^1$H NMR (300.13 MHz, CDCl$_3$) δ(ppm) 7.36-7.50 (m, 1H) 7.69-7.79 (m, 2H) 10.51 (s, 1H) 10.57 (s, 1H). $^{19}$F NMR (282.38 MHz, CDCl$_3$) δ(ppm) −118.90 (s).

10c. Synthesis of 1,8-difluoro-6,13-pentacenequinone—Compound 17 and 1,11-difluoro-6,13-pentacenequinone—Compound 18

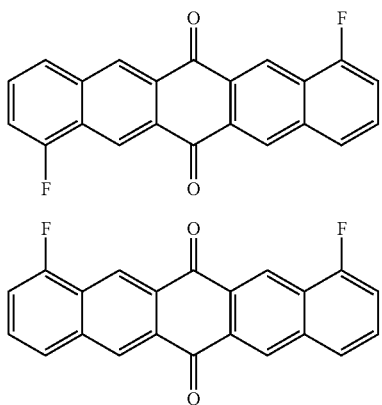

Compound 17

Compound 18

To a solution of 3-fluorophthalaldehyde (Compound 18) (0.42 g, 2.8 mmol, 2 molar equivalents) and 1,4-cyclohexanedione (0.15 g, 1.4 mmol, 1 molar equivalent) in ethanol (45 ml) was added a solution of 5% aqueous NaOH (0.6 ml) at room temperature. The reaction mixture was stirred 30 minutes at room temperature and then warmed to 60° C. After 1 hour at 60° C., the reaction mixture was cooled to room temperature. The resulting precipitate was filtered, washed with water (15 ml), ethanol (30 ml) and diethyl ether (30 ml) to give the title compounds as a yellow powder (0.40 g, 87%) used as obtained. $^1$H NMR (300.13 MHz, CDCl$_3$, trifluoroacetic acid) δ(ppm) 7.35-7.47 (m, 1H) 7.72 (td, J$_1$=8.03, J$_2$=5.32 Hz, 1H) 7.97 (d, J=8.22 Hz, 1H) 8.99-9.04 (m, 1H) 9.23-9.27 (m, 1H). $^{19}$F NMR (282.38 MHz, CDCl$_3$, trifluoroacetic acid) δ(ppm) −118.60 (s). IR (selected bands) 1681 (quinone), 1627, 1443, 1287, 791, 747 cm$^{-1}$,

10d. Synthesis of 1,8-difluoro-6,13-bis(triisopropylsilylethynyl)pentacene—Compound 19 and 1,11-difluoro-6,13-bis(triisopropylsilylethynyl)pentacene—Compound 20

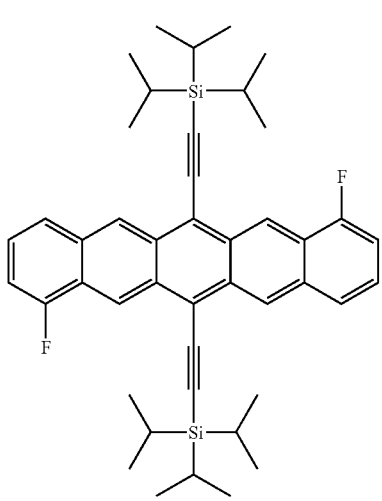

Compound 19

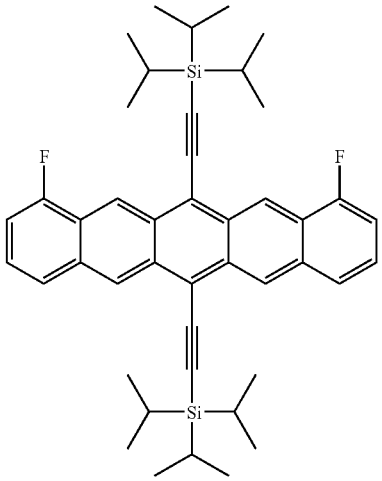

Compound 20

To a solution of triisopropylsilylacetylene (1.2 m, 5.3 mmol, 6 molar equivalents) in THF (30 ml) cooled to −78° C. was added dropwise a 2.5M solution of n-butyllithium in hexane (1.9 ml, 4.8 mmol, 5.5 molar equivalents). The solution was then stirred at −78° C. for 45 minutes and the difluoro-6,13-pentacenequinones (Compounds 17 and 18) (0.3 g, 0.9 mmol, 1 molar equivalent) added. The reaction mixture was then warmed up and stirred overnight at room temperature. A solution of 10% aqueous HCl saturated with SnCl$_2$ (3 ml) was added at room temperature and the reaction mixture was stirred at 50° C. for 45 minutes. On cooling, a solution of 2M aqueous solution of Na$_2$CO$_3$ (3 ml) was added. The resulting solution was filtered through celite and concentrated under vacuum to give a dark red solid. Purification by column chromatography on silica gel (eluent, hexane:DCM 9:1) followed by an acetone wash gave the title compounds as a dark blue powder (0.38 g, 65%) greater than 99% pure by HPLC (Syn and anti isomers co-elute). $^1$H NMR (500.13 MHz, CDCl$_3$) δ (ppm) 1.35-1.39 (m, 42H) 7.03-7.09 (m, 2H) 7.25-7.37 (m, 2H) 7.77 (d, J=8.77 Hz, 2H) 9.33 (s, 2H) 9.60 (s, 2H); $^{13}$C NMR (75.48 MHz, CDCl$_3$) δ(ppm) 11.64, 18.88, 18.93, 104.10, 104.24, 107.71, 107.75, 108.02, 108.24, 120.27, 124.62, 125.27, 125.37, 126.35, 126.47, 130.43, 130.88, 157.27, 160.67.

11. Synthesis of 2,3,9,10-tetrafluoro-6,13-bis(triisopropylsilylethynyl)pentacene—Compound 24

11a. Synthesis of 4,5-Difluorobenzene-1,2-dimethanol—Compound 21

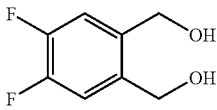

Compound 21

To a solution of LiAlH$_4$ (1M in tetrahydrofuran) (11 ml, 11.0 mmol, 2.0 molar equivalents) cooled to −78° C. was added dropwise a solution of 4,5-difluorophtalic anhydride (1.0 g, 5.4 mmol, 1 molar equivalent) in THF (5 ml). The reaction mixture was allowed to warm up to room temperature and then stirred at 70° C. for 2 hours. To this resulting solution cooled to 0° C. was added a 2M sodium hydroxide solution (5 ml) followed by cold water (5 ml) and THF (10 ml). The reaction mixture was then further extracted with THF (3 times 20 ml). The organic fractions were combined, washed with brine, dried over magnesium sulfate, filtered and concentrated in vacuum to give a light yellow solid. Purification by recrystallisation from acetone/hexane gave the title compound as light yellow needles (0.8 g, 85%). $^1$H NMR (300.13 MHz, DMSO) δ(ppm) 4.47 (d, J=5.30, 4H) 5.26 (t, J=5.30 Hz, 2H) 7.36 (t, J=10.10 Hz, 2H). $^{19}$F NMR (282.38 MHz, DMSO) δ(ppm) −142.27 (s).

11b. Synthesis of 4,5-Difluorophthalaldehyde—Compound 22

Compound 22

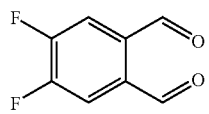

To a solution of oxalyl chloride 2M in dichloromethane (DCM) (4.5 ml, 8.8 mmol, 2.2 molar equivalents) cooled to −78° C. was added dropwise a solution of dimethylsulfoxyde (DMSO) (1.25 ml, 17.7 mmol, 4.4 molar equivalents) in DCM (5 ml). The solution was stirred at −78° C. for 5 minutes and 4,5-difluorobenzene-1,2-dimethanol (compound 21) (0.70 g, 4.0 mmol, 1.0 molar equivalent) dissolved in a mixture of DCM/DMSO (1-2 ml) was added dropwise. The solution was stirred for 1 hour at −78° C. and triethylamine (15 ml) was slowly added at −78° C. The reaction mixture was stirred for 10 minutes at −78° C. and slowly warmed up to room temperature. Ice-cold water (25 ml) was added to the reaction mixture and the aqueous layer extracted with DCM (3 times 30 ml). The organic fractions were combined, dried over magnesium sulfate, filtered and concentrated in vacuum to give a yellow oil. Purification by column chromatography on silica gel (eluent, hexane:DCM 2:8) gave the title compound as a light yellow solid (0.58 g, 85%). $^1$H NMR (300.13 MHz, CDCl$_3$) δ(ppm) 7.83 (t, J=9.00 Hz, 2H) 10.49 (s, 2H). $^{19}$F NMR (282.38 MHz, CDCl$_3$) δ(ppm) −127.10 (s).

11c. Synthesis of 2,3,9,10-tetrafluoro-6,13-pentacenequinone—Compound 23

Compound 23

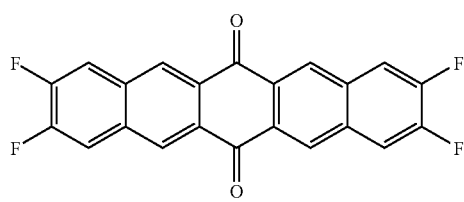

To a solution of 4,5-difluorophthalaldehyde (Compound 22) (0.48 g, 2.8 mmol, 2 molar equivalents) and 1,4-cyclohexanedione (0.16 g, 1.4 mmol, 1 molar equivalent) in ethanol (40 ml) was added a solution of 5% aqueous NaOH (0.6 ml) at room temperature. The reaction mixture was stirred for 30 minutes at room temperature and then warmed to 60° C. After 1 hour at 60° C., the reaction mixture was cooled to room temperature. The resulting precipitate was filtered, washed with water (15 ml), ethanol (30 ml) and diethyl ether (30 ml) to give the title compound as a yellow powder (0.35 g, 64%) used as obtained.

11d. Synthesis of 2,3,9,10-tetrafluoro-6,13-bis(triisopropylsilylethynyl)pentacene—Compound 24

Compound 24

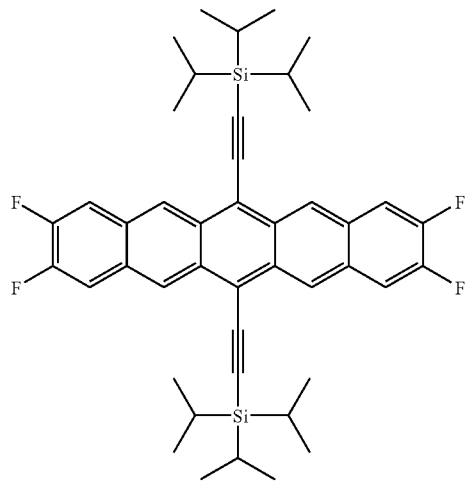

To a solution of triisopropylsilylacetylene (0.7 ml, 3.2 mmol, 6 molar equivalents) in THF (20 ml) cooled to −78° C. was added dropwise a 2.5M solution of n-butyllithium in hexane (1.2 ml, 2.9 mmol, 5.5 molar equivalents). The solution was stirred at −78° C. for 45 minutes followed by the addition of 2,3,9,10-tetrafluoro-6,13-pentacenequinone (Compound 23) (0.2 g, 0.5 mmol, 1 molar equivalent). The reaction mixture was then allowed to warm up to room temperature overnight. A solution of 10% aqueous HCl saturated with SnCl$_2$ (2 ml) was added at room temperature and the reaction mixture was stirred at 50° C. for 45 minutes. On cooling, a solution of 2M aqueous solution of Na$_2$CO$_3$ (2 ml) was added. The resulting solution was filtered through celite and concentrated under vacuum to give a dark blue solid. Purification by column chromatography on silica gel (eluent, hexane:DCM 9:1) followed by an acetone wash gave the title compound as a dark blue powder (0.13 g, 35%). $^1$H NMR (300.13 MHz, CDCl$_3$) δ (ppm) 1.32-1.44 (m, 42H) 7.63 (t, J=9.00 Hz, 4H) 9.20 (t, 4H); $^{19}$F NMR (282.38 MHz, CDCl$_3$) δ(ppm) −134.01 (s).

Examples 12 to 15

Mobility Measurements for OFETs Prepared in the Absence and Presence of a (Polymeric) Binder Determination of the Field Effect Mobility The field effect mobility of the following organic semiconductor materials was tested using the techniques described by Holland at al, J. Appl. Phys. Vol. 75, p. 7954 (1994).

In the following examples a test field effect transistor was manufactured by using a PEN substrate upon which were patterned Pt/Pd source and drain electrodes by standard techniques, for example shadow masking. Semiconductor formulations were prepared using compound 1 (example 12) and compound 4 (example 14) blended with an inert polymeric binder resin (poly(alpha-methylstyrene) (ρ-αMS)). The semiconductor formulations were then dissolved one part into 99 parts of solvent (toluene for examples 12 and 13, 1,2-dichlorobenzene for examples 14 and 15), and spin coated onto the substrate at 500 rpm for 18 seconds. To ensure complete drying, the samples were placed in an oven for 20 minutes at 100° C. For comparison, films of the pure organic semiconductor compound (OSC) in the absence of binder were coated onto the substrates by spin coating (comparative example 13 for compound 1 and comparative example 15 for compound 4). These samples were then also dried in an oven for 20 minutes at 100° C. The insulator material (Cytop 107M, available from Asahi Glass) was mixed 3 parts to 2 parts of perfluorosolvent (FC75, Acros catalogue number 12380) and then spin-coated onto the semiconductor giving a thickness typically of approximately 1 μm. The samples were placed once more in an oven at 100° C. for 20 minutes to evaporate solvent from the insulator. A gold gate contact was defined over the device channel area by evaporation through a shadow mask. To determine the capacitance of the insulator layer a number of devices were prepared which consisted of a non-patterned Pt/Pd base layer, an insulator layer prepared in the same way as that on the FET device, and a top electrode of known geometry. The capacitance was measured using a hand-held multimeter, connected to the metal either side of the insulator. Other defining parameters of the transistor are the length of the drain and source electrodes facing each other (W=30 mm) and their distance from each other (L=130 μm).

The voltages applied to the transistor are relative to the potential of the source electrode. In the case of a p-type gate material, when a negative potential is applied to the gate, positive charge carriers (holes) are accumulated in the semiconductor on the other side of the gate dielectric. (For an n-channel FET, positive voltages are applied). This is called the accumulation mode. The capacitance per unit area of the gate dielectric $C_I$ determines the amount of the charge thus induced. When a negative potential $V_{DS}$ is applied to the drain, the accumulated carriers yield a source-drain current $I_{DS}$ which depends primarily on the density of accumulated carriers and, importantly, their mobility in the source-drain channel. Geometric factors such as the drain and source electrode configuration, size and distance also affect the current. Typically a range of gate and drain voltages are scanned during the study of the device. The source-drain current is described by Equation 1.

$$I_{DS} = \frac{\mu W C_I}{L}\left((V_G - V_0)V_{DS} - \frac{V_{DS}^2}{2}\right) + I_\Omega, \quad \text{Equation 1}$$

where $V_0$ is an offset voltage and $I_\Omega$ is an ohmic current independent of the gate voltage and is due to the finite conductivity of the material. The other parameters have been described above.

For the electrical measurements the transistor sample was mounted in a sample holder. Microprobe connections were made to the gate, drain and source electrodes using Karl Suss PH100 miniature probe-heads. These were linked to a Hewlett-Packard 4155B parameter analyser. The drain voltage was set to −5 V and the gate voltage was scanned from +20 to −60V and back to +20V in 1 V steps. In accumulation, when $|V_G|>|V_{DS}|$ the source-drain current varies linearly with $V_G$. Thus the field effect mobility can be calculated from the gradient (S) of $I_{DS}$ vs. $V_G$ given by Equation 2.

$$S = \frac{\mu W C_I V_{DS}}{L} \quad \text{Equation 2}$$

All field effect mobilities quoted below were calculated using this regime (unless stated otherwise). Where the field effect mobility varied with gate voltage, the value was taken as the highest level reached in the regime where $|V_G|>|V_{DS}|$ in accumulation mode. The values quoted in Table 4 are an average taken over several devices (fabricated on the same substrate), the sample size for the number of devices tested is also quoted in Table 4. An example of the current-voltage and mobility-voltage characteristics for Example 12 is shown in FIG. 1. The forward and reverse scans illustrate the low current hysteresis of the device. The results show the excellent charge mobility of OFET devices when a binder is used with the organic semiconductor material tested. When a binder is not used, there is considerable variation in the mobility measured for devices coated on the same substrate. This fact is reflected in the large standard deviation (as a % of the mean value) of the mobility values for the OFETs coated on the same substrate.

TABLE 4

OFET performance of semiconductor formulations prepared with and without binder material

| Example number | Organic Semiconducting Material (OSC) | OSC and binder solids content in coating solution (by weight) | Binder | OSC:Binder Ratio (wt:wt) | Mobility [cm²/Vs] (+/−1 std. dev.) | Sample Size |
|---|---|---|---|---|---|---|
| 12 | Compound 1 (example 1) | 1% | p-αMS | 50:50 | 0.433 (+/−0.19) | 9 |
| 13 (comparative) | Compound 1 | 1% | — | 100:0 | 0.14 (+/−0.14) | 6 |
| 14 | Compound 4 (example 3) | 1% | p-αMS | 50:50 | 1.1 (+/−0.4) | 15 |
| 15 (comparative) | Compound 4 | 1% | — | 100:0 | 0.11 (+/−0.14) | 7 |

The results in Table 4 demonstrate that there is a substantial improvement in the mobility values and uniformity of OFETs when a (polymeric) binder is used in a formulation for an OFET device. The improvement in uniformity is illustrated by the small standard deviation (Std. dev) of the mobility results as a proportion of the mean value for the examples with binder (examples 12 and 14). This is in contrast to examples 13 and 15 were no binder was employed which show a large standard deviation (as a proportion of the mean value).

Examples 16 to 26

Mobility Measurements for OFETs Prepared Using a Range of Polymeric Binders

OFETs were prepared using the method as described for examples 12 to 15 with the exception that different polymeric binders were used.

TABLE 5

Mobility measurements for OFETs prepared using a range of polymeric binders

| Example number | Organic semi-conducting material (OSC) | Binder mixed at 1:1 (by weight) with polyacene | OSC & binder solids content in coating solution (by weight) | Solvent | Mobility [cm$^2$/Vs] (+/−1 std. dev.) | Sample size | Permittivity of binder ε 1 kHz |
|---|---|---|---|---|---|---|---|
| 12 | Compound 1 | p-αMS | 1% | toluene | 0.433 (+/−0.19) | 9 | 2.6$^a$ |
| 14 | Compound 4 | p-αMS | 1% | 1,2-Dichloro-benzene | 1.1 (+/−0.4) | 15 | 2.6$^a$ |
| 16 | Compound 1 | Topas 8007 | 4% | Ethylcyclohexane | 0.26 (+/−0.090) | 7 | 2.2-2.3$^b$ |
| 17 | Compound 1 | Topas 8007 | 4% | Anisole | 0.26 (+/−0.082) | 5 | 2.2-2.3$^b$ |
| 18 | Compound 1 | PS (1M) | 4% | p-xylene | 0.20 (+/−0.085) | 8 | 2.5$^a$ |
| 19 | Compound 1 | p-4-MS | 4% | p-xylene | 0.26 (+/−0.11) | 5 | 2.7$^c$ |
| 20 | Compound 1 | PS-co-αMS | 4% | p-xylene | 0.21 (+/−0.19) | 5 | 2.5-2.6$^a$ |
| 21 | Compound 4 | poly(vinyl-cinnamate) | 1% | 1,2-Dichloro-benzene | 1.4 ± 0.47 | 8 | 2.9$^c$ |
| 22 (comparative) | Compound 1 | PMMA | 4% | Acetone | 0.0029 (+/−0.0025) | 6 | 3.5$^d$ |
| 23 (comparative) | Compound 1 | PVP | 1% | Acetone | No FET mobility was observed | | 4.5$^e$ |
| 24 (comparative) | Compound 1 | PVA | 1% | Acetone | No FET mobility was observed | | 10.4$^a$ |
| 25 | Compound 4 | poly(4-vinylbiphenyl) | 1% | 1,2-Dichloro-benzene | 1.0 ± 0.66 | 8 | 2.7$^c$ |
| 26 | Isomeric mixture of Compounds 19 and 20 | p-αMS | 1% | toluene | 0.16 (+/−0.025) | 4 | 2.6$^a$ |

Topa ™ 8007 - ex. Ticona (linear olefin and cycloolefin(norbornene)copolymer), (examples16 and 17);
PS (1M) - polystyrene M$_w$ = 1,000,000 Aldrich catalogue number 48,080-0, (example 18);
p-4-MS - poly-4-methylstyrene Aldrich catalogue number 18,227-3, (example 19)
PS-co-αMS - Polystyrene-co-alpha-methyl styrene Aldrich catalogue number 45,721-3, (example 20);
poly(vinylcinnamate) Aldrich No: 18,264-8, (example 21)
PMMA - polymethylmethacrylate Mn = 797, (example 22)
PVP - poly-4-vinylphenol Aldrich catalogue number 43,622-4, (comparative example 23);
PVA - polyvinylalcohol Aldrich catalogue number 35,316-2, (comparative example 24);
poly(4-vinylbiphenyl) Aldrich catalogue number 18,254-0, (example 25);
$^a$Polymer Handbook (3$^{rd}$ edition) Wiley and Sons (1989).
$^b$manufacturer's data
$^c$Obtained by measuring the capacitance and thickness of a film of binder between two metal electrodes and then calculating the dielectric constant ε using the relationship ε = Cd/E$_o$A where C is capacitance, d is the film thickness, E$_o$ is the permittivity of free space, and A is the area of the capacitor.
$^d$Ficker at al., J. Appl. Phys, 2003 94 (4), 2638.
$^e$Stutzman et al. Science 2003, 299, 1881.

The results in Table 5 illustrate that binders with a permittivity value greater than 3.3 lower the mobility value significantly in an OFET device. Therefore preferred polymeric binders have a permittivity value of less than 3.3.

Examples 27 to 28

OFETs were prepared using the method as described for examples 12 to 15 above with the exception that the polymeric binder used was a semiconducting material rather than an insulating binder. The results are illustrated in Table 6.

TABLE 6

Mobility measurements for OFETs prepared using a semiconducting binder

| Example number | Organic semi-conducting material (OSC) | Binder mixed at 1:1 (by weight) with polyacene | OSC and binder solids content in coating solution (by weight) | Solvent | Mobility [cm$^2$/Vs] (+/−1 std. dev.) | Sample size | Permittivity of semiconducting binder ε at 1 kHz |
|---|---|---|---|---|---|---|---|
| 27 | Compound 4 | poly(9-vinylcarbazol) | 1% | 1,2-Dichlorobenzene | 1.44 ± 0.35 | 7 | 2.7 |
| 28 | Compound 1 | PTAA1 | 4% | p-xylene | 0.28 (+/−0.09) | 7 | 2.9$^c$ |

In Table 6, the poly(9-vinylcarbazol) is available from Aldrich, catalogue number: 18,260-5 (example 27).
*—refers to Schaffert R. M. IBM Journal of Res. And Devel. Vol 15 No 1, p 79 (1971)
c—has the same meanings as in Table 5.
PTAA1—is a triarylamine compound of Formula 18.

Formula (18)

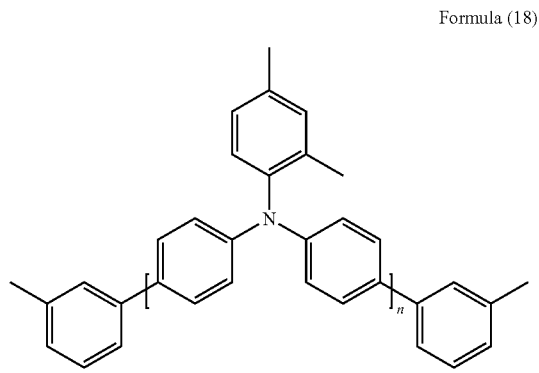

wherein n=10.7 and Mn=3100 (*Adv. Funct. Mater.* 2003, 13, No. 3. p 199-204)

The results in Table 6 illustrate that semiconducting binders may also be used to achieve OFET devices according to the present invention which demonstrate excellent mobility values.

Examples 29 to 31

OFETs were again prepared using the method as described for examples 12 to 15 above. However, in examples 29 to 31 the ratio of OSC material to binder was varied. Example 12 is also included for comparison.

TABLE 7

Mobility measurements for OFETs prepared with varying quantities of binder to OSC material

| Example number | Organic Semiconducting Material (OSC) | Binder | OSC and binder solids content in coating solution (by weight) | OSC:Binder Ratio (wt:wt) | Mobility [cm$^2$/Vs] | Sample Size |
|---|---|---|---|---|---|---|
| 12 | Compound 1 | p-αMS | 1% | 50:50 | 0.433 (+/−0.19) | 9 |
| 29 | Compound 1 | p-αMS | 1% | 75:25 | 0.321 (+/−0.11) | 7 |
| 30 | Compound 1 | p-αMS | 1% | 90:10 | 0.327 (+/−0.11) | 6 |
| 31 | Compound 1 | p-αMS | 1% | 95:5 | 0.244 (+/−0.077) | 8 |

The above results illustrate that excellent mobility values can be obtained for an OFET device even when the ratio of OSC material to binder is 50:50.

Examples 32 to 35

Mobility Measurements for OFETs Prepared with a Variation in the Solids Content

OFETs were again prepared using the method as described for examples 12 to 15 above with the exception that the solids content of the formulation was varied.

TABLE 8

Variation of the solids content in a coating solution used to prepare an OFET

| Example number | Organic semiconducting material (OSC) | Binder mixed at 1:1 (by weight) with polyacene | OSC and binder solids content in coating solution (by weight) | Mobility [cm$^2$/Vs] (+/−1 std. dev.) | Sample size |
|---|---|---|---|---|---|
| 32 | Compound 1 | p-αMS | 0.5% | 0.29 (+/−0.23) | 9 |
| 33 | Compound 1 | p-αMS | 1% | 0.40 (+/−0.14) | 11 |
| 34 | Compound 1 | p-αMS | 2% | 0.39 (+/−0.15) | 11 |
| 35 | Compound 1 | p-αMS | 4% | 0.53 (+/−0.07) | 11 |

Figure 1:
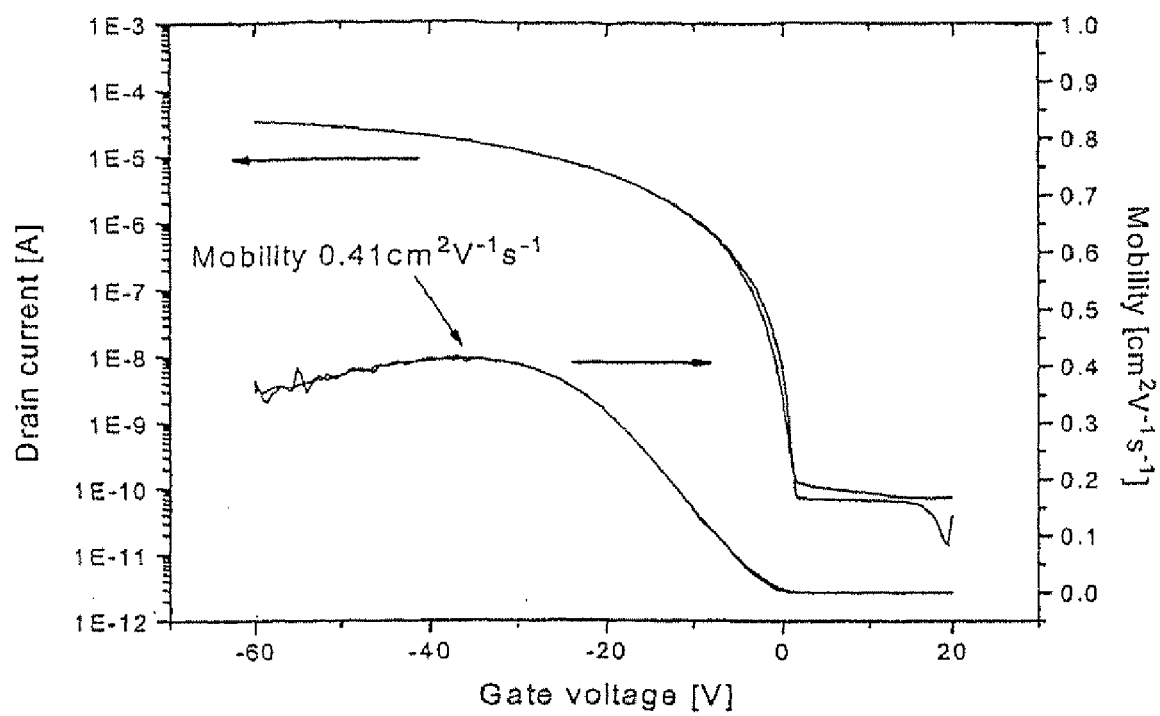
FIG. 1 schematically depicts the results of example 12.

The invention claimed is:

1. An organic semiconducting layer formulation, comprising an organic binder which has a permittivity, $\in$, at 1,000 Hz of 3.3 or less; and a polyacene compound of formula 9

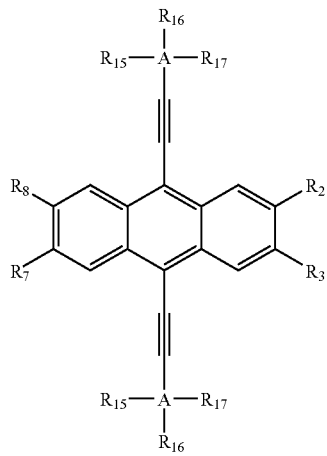

Formula 9 wherein $R_2$, $R_3$, $R_7$, $R_8$, $R_{15}$, $R_{16}$, and $R_{17}$ each independently is the same or different and each independently represents: H; an optionally substituted $C_1$-$C_{40}$ carbyl or hydrocarbyl group; an optionally substituted $C_1$-$C_{40}$ alkoxy group; an optionally substituted $C_6$-$C_{40}$ aryloxy group; an optionally substituted $C_7$-$C_{40}$ alkylaryloxy group; an optionally substituted $C_2$-$C_{40}$ alkoxycarbonyl group; an optionally substituted $C_7$-$C_{40}$ aryloxycarbonyl group; a cyano group (—CN); a carbamoyl group (—C(=O)NH$_2$); a haloformyl group (—C(=O)—X, wherein X represents a halogen atom); a formyl group (—C(=O)—H); an isocyano group; an isocyanate group; a thiocyanate group or a thioisoeyanate group; an optionally substituted amino group; an hydroxy group; a nitro group; a CF$_3$ group; a halo group; or an optionally substituted silyl group; and wherein independently each pair of $R_2$ and $R_3$, $R_7$ and $R_8$, $R_{15}$ and $R_{16}$, and $R_{16}$ and $R_{17}$ is optionally cross-bridged with each other to form a $C_4$-$C_{40}$ saturated or unsaturated ring, which saturated or unsaturated ring is optionally interrupted by an oxygen atom, a sulphur atom or a group shown by formula: —N(R$_a$)— (wherein R$_a$ is a hydrogen atom or a hydrocarbon group), and is optionally substituted; wherein A represents silicon or germanium, and wherein one or more of the carbon atoms of the polyacene skeleton is optionally substituted by a heteroatom which is N, P, As, O, S, Se or Te, wherein at least one pair of $R_2$ and $R_3$, and $R_7$ and $R_8$, is cross-bridged with each other to form a $C_4$-$C_{40}$ saturated or unsaturated ring that is interrupted by an oxygen atom, a sulphur atom or a group shown by formula: —N(R$_a$)— (wherein R$_a$ is a hydrogen atom or a hydrocarbon group) and is optionally substituted.

2. An organic semiconducting layer formulation as claimed in claim 1, wherein the compound of formula 9 is of Formula 9A or its syn-isomer or formula 9B or its anti-isomer:

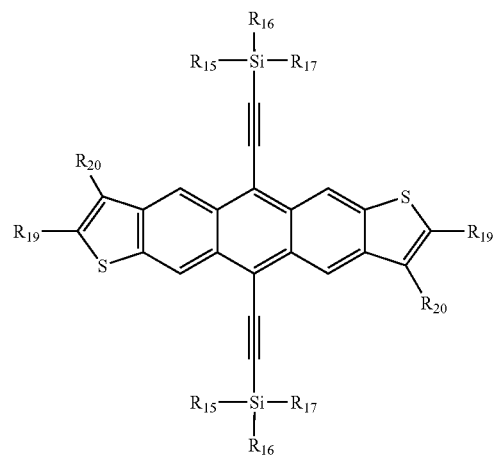

Formula 9A wherein $R_{19}$ and $R_{20}$ each independently is an optionally substituted, optionally unsaturated $C_{1-40}$ carbyl or hydrocarbyl group, or $R_{19}$ and $R_{20}$ either together with the carbon atoms to which they are attached or independently in combination with a substituent on a suitably adjacent atom form an optionally substituted $C_4$-$C_{40}$ saturated or unsaturated ring optionally interrupted by one or more oxygen or sulphur atoms or a group represented by Formula —N(R$_a$), wherein R$_a$ is a hydrogen atom or a hydrocarbon group, or $R_{19}$ and $R_{20}$ are the same substituent and comprise hydrogen or a saturated or unsaturated $C_{1-4}$-alkyl group, $R_{15}$, $R_{16}$, $R_{17}$ are the same or different and are as defined for the compound of formula 9, and one or more of the ring positions on the compound is optionally substituted;

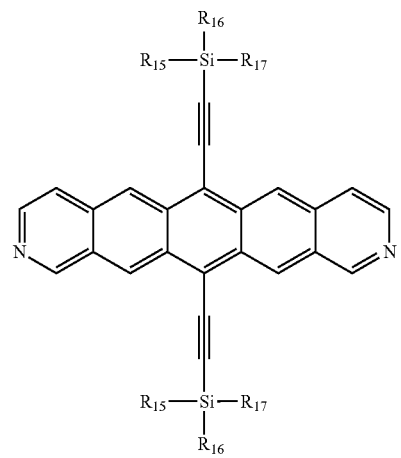

Formula 9B wherein $R_{15}$, $R_{16}$, $R_{17}$ are the same or different and are as defined for the compound of formula 9, and one or more of the ring positions on the compound is optionally substituted.

3. An organic semiconducting layer formulation as claimed in claim 1, wherein the organic binder resin has a permittivity at 1,000 Hz of less than 3.0.

4. An organic semiconducting layer formulation as claimed in claim 1, wherein the organic binder resin has a permittivity at 1,000 Hz greater than 1.7.

5. An organic semiconducting layer formulation as claimed in claim 1, wherein the organic binder resin is an insulating binder.

6. An organic semiconducting layer formulation as claimed in claim 1, wherein the organic binder resin is an insulating binder which is poly(α-methylstyrene), polyvinylcinnamate, poly(4-vinylbiphenyl), poly(4-methylstyrene) or linear olefin and cycloolefin(norbornene)copolymer.

7. An organic semiconducting layer formulation as claimed in claim 1, wherein the organic binder resin is a semiconductor binder.

8. An organic semiconducting layer formulation as claimed in claim 1, wherein the organic binder resin is a semiconductor binder which comprises a number average molecular weight ($M_n$) of at least 1500-2000.

9. An organic semiconducting layer formulation as claimed in claim 1, wherein the organic binder resin is a semiconductor binder which is poly(9-vinylcarbazole) or a triarylamine compound of the following formula

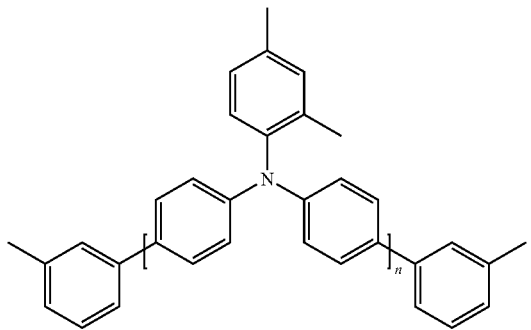

wherein n=10.7.

10. An organic semiconducting layer formulation as claimed in claim 1, wherein the formulation further comprises a solvent.

11. An organic semiconducting layer formulation as claimed in claim 1, wherein the formulation further comprises a solvent which is xylene(s), toluene, tetralin or odichlorobenzene.

12. An organic semiconducting layer formulation as claimed in claim 1, wherein the ratio of polyacence compound to binder is 20:1 to 1:20 by weight.

13. An organic semiconducting layer formulation as claimed in claim 1, which has a solids content of 0.1 to 10% by weight.

14. An organic semiconducting layer formulation as claimed in claim 2, wherein in the compound of Formula 9A
$R_2$ and $R_3$ and/or $R_7$ and $R_8$ together with the carbon atom to which they are attached form a $C_4$-$C_{40}$ saturated or unsaturated ring, that is optionally interrupted by one or more oxygen or sulphur atoms or by a group represented by the formula —$N(R_a)$ (wherein $R_a$ is a hydrogen atom or a hydrocarbon group), that is optionally substituted.

15. An organic semiconducting layer formulation as claimed in claim 2, wherein in the compound of Formula 9A
$R_2$ and $R_3$ and/or $R_7$ and $R_3$ together with the carbon atom to which they are attached form a $C_4$-$C_{10}$ unsaturated ring that is interrupted by one or more oxygen atoms, that is optionally substituted.

16. An organic semiconducting layer formulation as claimed in claim 14, wherein in the compound of Formula 9A
one or more of the carbon atoms of the polyacene skeleton is substituted by a heteroatom which is N, P, As, O, S, Se or Te.

17. An organic semiconducting layer formulation as claimed in claim 14, wherein in the compound of Formula 9A
$R_2$ and $R_3$ and/or $R_7$ and $R_8$ together with the carbon atom to which they are attached form a $C_4$-$C_{10}$ unsaturated ring that is interrupted by one or more oxygen atoms, which is substituted, wherein the substituents are selected from silyl, sulpho, sulphonyl, formyl, amino, imino, nitrilo, mercapto, cyano, nitro Cl, Br, or F.

18. An organic semiconducting layer formulation as claimed in claim 13, wherein in the compound of Formula 9A
$R_2$ and $R_3$ and/or $R_7$ and $R_8$ together with the carbon atom to which they are attached form a $C_4$-$C_{10}$ unsaturated ring that is interrupted by one or more sulphur atoms, that is optionally substituted.

19. An organic semiconducting layer formulation as claimed in claim 17, wherein in the compound of Formula 9A
one or more of the carbon atoms of the polyacene skeleton is substituted by a heteroatom which is N, P, As, O, S, Se or Te.

20. An organic semiconducting layer formulation as claimed in claim 17, wherein in the compound of Formula 9A
$R_2$ and $R_3$ and/or $R_7$ and $R_8$ together with the carbon atom to which they are attached form a $C_4$-$C_{10}$ unsaturated ring that is interrupted by one or more sulphur atoms, which is substituted, wherein the substituents are silyl, sulpho, sulphonyl, formyl, amino, imino, nitrilo, mercapto, cyano, nitro, Cl, Br or F.

21. An organic semiconducting layer formulation as claimed in claim 2, wherein in the compound of Formula 9A
$R_2$ and $R_3$ and/or $R_7$ and $R_8$ together with the carbon atom to which they are attached form a $C_4$-$C_{10}$ saturated or unsaturated ring that is interrupted by a group represented by the formula $N(R_a)$ (wherein $R_a$ is a hydrogen atom or a hydrocarbon group), which is optionally substituted.

22. An organic semiconducting layer formulation as claimed in claim 20, wherein in the compound of Formula 9A
one or more of the carbon atoms of the polyacene skeleton is substituted by a heteroatom which is N, P, As, O, S, Se or Te.

23. An organic semiconducting layer formulation as claimed in claim 20, wherein in the compound of Formula 9A
$R_2$ and $R_3$ and/or $R_7$ and $R_8$ together with the carbon atom to which they are attached form a $C_4$-$C_{10}$ saturated or unsaturated ring that is interrupted by a group represented by the formula —$N(R_a)$ (wherein $R_a$ is a hydrogen atom or a hydrocarbon group), which is substituted, wherein the substituents are silyl, sulpha, sulphonyl, formyl, amino, imino, nitrilo, mercapto, cyano, nitro Cl, Br or F.

24. An organic semiconducting layer formulation as claimed in claim 2, wherein in the compound of Formula 9B
one or more of the carbon atoms of the polyacene skeleton is substituted by a heteratom which is N, P, As, O, S, Se or Te.

25. An organic semiconducting layer formulation as claimed in claim 24, wherein in the compound of Formula 9B
$R_{19}$ and $R_{20}$ are each independently optionally substituted, saturated or unsaturated, cyclic or acyclic $C_{1-40}$ carbyl or hydrocarbyl groups or F, Cl or Br.

26. An organic semiconducting layer formulation as claimed in claim 25, wherein in the compound of Formula 9B the carbyl or hydrocarbyl groups are each independently a $C_1$-$C_{40}$ alkyl group, a $C_{2\text{-}40}$ alkenyl group, a $C_2$-$C_{40}$ alkynyl group, a $C_3$-$C_{40}$ alkyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, or a $C_4$-$C_{40}$ cycloalkenyl group, all of which are optionally substituted.

27. An organic semiconducting layer formulation as claimed in claim 26, wherein in the compound of Formula 9B the carbyl or hydrocarbyl groups are each independently a $C_1$-$C_{10}$ alkyl group, a $C_2$-$C_{10}$ alkenyl group, a $C_2$-$C_{10}$ alkynyl group, a $C_3$-$C_{10}$ alkyl group, a $C_4$-$C_{10}$ alkyldienyl group, a $C_6$-$C_{12}$ aryl group or a $C_4$-$C_{10}$ polyenyl group, all of which are optionally substituted.

28. An organic semiconducting layer formulation as claimed in claim 26, wherein in the compound of Formula 9B the substituents are silyl, sulpho, sulphonyl, formyl, amino, imino, nitrilo, mercapto, cyano, nitro, Cl, Br or F.

29. An organic semiconducting layer formulation as claimed in claim 26, wherein in the compound of Formula 9 $R_2$ and $R_3$ and/or $R_7$ and $R_8$ together with the carbon atom to which they are attached form a $C_4$-$C_{40}$ saturated or unsaturated ring, that is optionally interrupted by one or more oxygen or sulphur atoms or by a group represented by the formula —$N(R_a)$ (wherein $R_a$ is a hydrogen atom or a hydrocarbon group), that is optionally substituted.

30. An organic semiconducting layer formulation as claimed in claim 29, wherein in the compound of Formula 9 $R_2$ and $R_3$ and/or $R_7$ and $R_8$ together with the carbon atom to which they are attached form a $C_4$-$C_{10}$ unsaturated ring that is interrupted by one or more oxygen atoms, that is optionally substituted.

31. An organic semiconducting layer formulation as claimed in claim 30, wherein in the compound of Formula 9 one or more of the carbon atoms of the polyacene skeleton is substituted by a heteroatom which is N, P, As, O, S, Se or Te.

32. An organic semiconducting layer formulation as claimed in claim 30, wherein in the compound of Formula 9 $R_2$ and $R_3$ and/or $R_7$ and $R_8$ together with the carbon atom to which they are attached form a $C_4$-$C_{10}$ unsaturated ring that is interrupted by one or more oxygen atoms, which is substituted, wherein the substituents are selected from silyl, sulpho, sulphonyl, formyl, amino, imino, nitrilo, mercapto, cyano, nitro Cl, Br, or F.

33. An organic semiconducting layer formulation as claimed in claim 29, wherein in the compound of Formula 9 $R_2$ and $R_3$ and/or $R_7$ and $R_8$ together with the carbon atom to which they are attached form a $C_4$-$C_{10}$ unsaturated ring that is interrupted by one or more sulphur atoms, that is optionally substituted.

34. An organic semiconducting layer formulation as claimed in claim 33, wherein in the compound of Formula 9 one or more of the carbon atoms of the polyacene skeleton is substituted by a heteroatom which is N, P, As, O, S, Se or Te.

35. An organic semiconducting layer formulation as claimed in claim 33, wherein in the compound of Formula 9 $R_2$ and $R_3$ and/or $R_7$ and $R_8$ together with the carbon atom to which they are attached form a $C_4$-$C_{10}$ unsaturated ring that is interrupted by one or more sulphur atoms, which is substituted, wherein the substituents are silyl, sulpho, sulphonyl, formyl, amino, imino, nitrilo, mercapto, cyano, nitro, Cl, Br or F.

36. An organic semiconducting layer formulation as claimed in claim 29, wherein in the compound of Formula 9 $R_2$ and $R_3$ and/or $R_7$ and $R_8$ together with the carbon atom to which they are attached form a $C_4$-$C_{10}$ saturated or unsaturated ring that is interrupted by a group represented by the formula —$N(R_a)$ (wherein $R_a$ is a hydrogen atom or a hydrocarbon group), which is optionally substituted.

37. An organic semiconducting layer formulation as claimed in claim 36, wherein in the compound of Formula 9 one or more of the carbon atoms of the polyacene skeleton is substituted by a heteroatom which is N, P, As, O, S, Se or Te.

38. An organic semiconducting layer formulation as claimed in claim 36, wherein in the compound of Formula 9 $R_2$ and $R_3$ and/or $R_7$ and $R_8$ together with the carbon atom to which they are attached form a $C_4$-$C_{10}$ saturated or unsaturated ring that is interrupted by a group represented by the formula —$N(R_a)$ (wherein $R_a$ is a hydrogen atom or a hydrocarbon group), which is substituted, wherein the substituents are silyl, sulpho, sulphonyl, formyl, amino, imino, nitrilo, mercapto, cyano, nitro Cl, Br or F.

39. In an electronic device, wherein the improvement comprises the presence of an organic semiconducting layer in said electronic device, which organic semiconducting layer comprises an organic semiconducting layer formulation as claimed in claim 1.

40. A field effect transistor (FET), organic light emitting diode (OLED), photodetector, chemical detector, photovoltaic cell (PVs), capacitor sensor, logic circuit, display or memory device, comprising an organic semiconducting layer, which comprises an organic semiconducting layer formulation as claimed in claim 1.

41. An OFET device, comprising an organic semiconducting layer formulation as claimed in claim 1,
wherein the binder is poly(α-methylstyrene), linear olefin and cycloolefin(norbornene)copolymer, poly(4-methylstyrene), polystyrene or polystyrene-co-α-methylstyrene; and
which formulation further comprises a solvent which is toluene, ethylcyclohexane, anisole or pxylene.

42. A process for preparing an organic semiconducting layer formulation as claimed in claim 1, comprising (i) depositing on a substrate a liquid layer of a mixture which comprises the polyacene compound, the organic binder resin or precursor thereof and optionally a solvent, and (ii) forming from the liquid layer a solid layer which is the organic semiconducting layer.

* * * * *

UNITED STATES PATENT AND TRADEMARK OFFICE
CERTIFICATE OF CORRECTION

PATENT NO.        : 8,119,804 B2
APPLICATION NO.   : 12/719545
DATED             : February 21, 2012
INVENTOR(S)       : Beverly Anne Brown et al.

It is certified that error appears in the above-identified patent and that said Letters Patent is hereby corrected as shown below:

Column 56, line 53 (Claim 23), reads: "wherein the substituents are silyl, sulpha, sulphonyl,"
It should read: -- wherein the substituents are silyl, sulpho, sulphonyl, --

Column 57, line 12 (Claim 27), reads: "alkynyl group, a $C_3$-$C_{10}$ alkyl group, a $C_4$-$C_{10}$ alkyldie-"
It should read: -- alkynyl group, a $C_3$-$C_{10}$ allyl group, a $C_4$-$C_{10}$ alkyldie- --.

Signed and Sealed this
Twenty-ninth Day of May, 2012

David J. Kappos
*Director of the United States Patent and Trademark Office*